US011052150B2

(12) United States Patent
Yasuda et al.

(10) Patent No.: US 11,052,150 B2
(45) Date of Patent: Jul. 6, 2021

(54) METHOD AND PHARMACEUTICAL COMPOSITION FOR TREATING CROHN'S DISEASE

(71) Applicant: Eisai R&D Management Co., Ltd., Tokyo (JP)

(72) Inventors: Nobuyuki Yasuda, Tsukuba (JP); Kiyoshi Oketani, Tokyo (JP); Hiroko Baba, Tokyo (JP); Tomohisa Nakano, Tokyo (JP); Masahiko Mori, Tokyo (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 48 days.

(21) Appl. No.: 15/951,321

(22) Filed: Apr. 12, 2018

(65) Prior Publication Data
US 2018/0303933 A1    Oct. 25, 2018

(30) Foreign Application Priority Data
Apr. 14, 2017    (JP) .............................. JP2017-080317

(51) Int. Cl.
| A61K 39/395 | (2006.01) |
| A61K 39/00 | (2006.01) |
| A61P 1/00 | (2006.01) |
| C07K 16/24 | (2006.01) |
| A61K 9/00 | (2006.01) |

(52) U.S. Cl.
CPC ............ *A61K 39/3955* (2013.01); *A61P 1/00* (2018.01); *C07K 16/24* (2013.01); *A61K 9/0019* (2013.01); *A61K 2039/505* (2013.01); *A61K 2039/54* (2013.01); *A61K 2039/545* (2013.01); *C07K 2317/24* (2013.01); *C07K 2317/52* (2013.01); *C07K 2317/71* (2013.01); *C07K 2317/94* (2013.01)

(58) Field of Classification Search
None
See application file for complete search history.

(56) References Cited

U.S. PATENT DOCUMENTS

2003/0027843 A1 * 2/2003 Yotsuya ................. A61K 31/44
514/336

FOREIGN PATENT DOCUMENTS

| EP | 3211007 | 8/2017 |
| JP | 2018065796 | 4/2018 |
| WO | 2006/046739 | 5/2008 |
| WO | 2011/052799 | 5/2011 |

OTHER PUBLICATIONS

Cole et al. (1997, J. Immunol. 159:3613-3621).*
Tabuchi et al., "First-in-Human (FIH) Study of E6011, a Novel Humanized Anti-Fractalkine (CX3CL1) Monoclonal Antibody," Annual Meeting of the American-Society-for-Clinical-Pharmacology-and-Therapeutics, *ASCPT,* Clinical Pharmacology and Therapeutics, Feb. 2016, 99(1):s33, Abstract PI-008.
"Efficacy and safety of anti-fractalkine monoclonal antibody, E6011, in patients with Crohn's disease who had lost response to anti-TNFα agents: A multicentre, open-label, Phase 1/2 study," *European Crohn's and Colitis Organisation,* Feb. 2018, 7 pages.
European Extended Search Report in European Application No. 17157844.6, dated May 19, 2017, 6 pages.
Matsuoka et al., "Safety, Tolerability and Efficacy of E6011, Anti-Human Fractalkine Monoclonal Antibody, in the First-in-Patient Study for Crohn's Disease," Gastroenterology, Apr. 2016, 150(4):S-808, Abstract Mo1890.
Matsuoka et al., "Safety, Tolerability and Efficacy of E6011, Anti-Human Fractalkine Monoclonal Antibody, in the First-in-Patient Study for Crohn's Disease," *Digestive Disease Week Archives,* Abstract, May 2016, Abstract Mo1890, 3 pages.
Matsuoka et al., "Efficacy and safety of anti-fractalkine monoclonal antibody, E6011, in patients with Crohn's disease who had lost response to anti-TNFα agents: A multicentre, open-label, Phase 1/2 study," *Journal of Crohn's and Colitis,* Jan. 2018, 12(1):S070.
Matsuoka et al., "Safety, Tolerability and Efficacy of E6011, Anti-Human Fractalkine Monoclonal Antibody, in the First-in-Patient Study for Crohn's Disease," Poster presented at Digestive Disease Week 2016 Archives, May 2016.
Nishimura et al., "Chemokines as Novel Therapeutic Targets for Inflammatory Bowel Disease," New York Academy of Sciences, 2009, 1173:350-356.
Tanaka et al., "Safety and Efficacy of E6011, an Anti-Human Fractalkine Monoclonal Antibody, in a First-in-Patient Phase 1/2 Study in Rheumatoid Arthritis," Arthritis & Rheumatology (Hoboken) John Wiley & Sons Inc., Oct. 2015, 67(10).

(Continued)

*Primary Examiner* — Elizabeth C. Kemmerer
(74) *Attorney, Agent, or Firm* — Fish & Richardson P.C.

(57) ABSTRACT

It is an object of the present invention to provide a pharmaceutical composition comprising an anti-fractalkine antibody that provides therapeutically effective improvement to Crohn's disease, after the administration thereof to a human subject, and a method for treating Crohn's disease. Provided is a pharmaceutical composition for treating Crohn's disease. The present pharmaceutical composition comprises an anti-fractalkine antibody and a pharmaceutically acceptable excipient, and is used, such that the anti-fractalkine antibody is intravenously administered to a human at a dose of at least 10 mg/kg of human body weight in a method for treating Crohn's disease.

7 Claims, 5 Drawing Sheets
Specification includes a Sequence Listing.

(56) References Cited

OTHER PUBLICATIONS

Office Action in European Patent Application No. 17157844.6, dated Sep. 6, 2019, 5 pages.
Response and Amended Claims in European Patent Application No. 17157844.6, dated Dec. 17, 2019, 13 pages.
Shi et al., "The state of the art on treatment of Crohn's disease," Journal of Gastroenterology, 2018, 53:989-998.
EP Response and Amended Claims in European Patent Application No. 17157844.6, dated Feb. 3, 2021, 16 pages.
EP Response, Amended Claims, and Adapted Description in European Patent Application No.17157844.6, dated Mar. 3, 2021, 185 pages.
EP Result of consultation in European Patent Application No. 17157844.6, dated Mar. 4, 2021, 3 pages.
EP Summons to attend oral proceedings pursuant to Rule 115(1) EPC in European Patent Application No. 17157844.6, dated Aug. 11, 2020, 8 pages.

* cited by examiner

[FIG. 1]

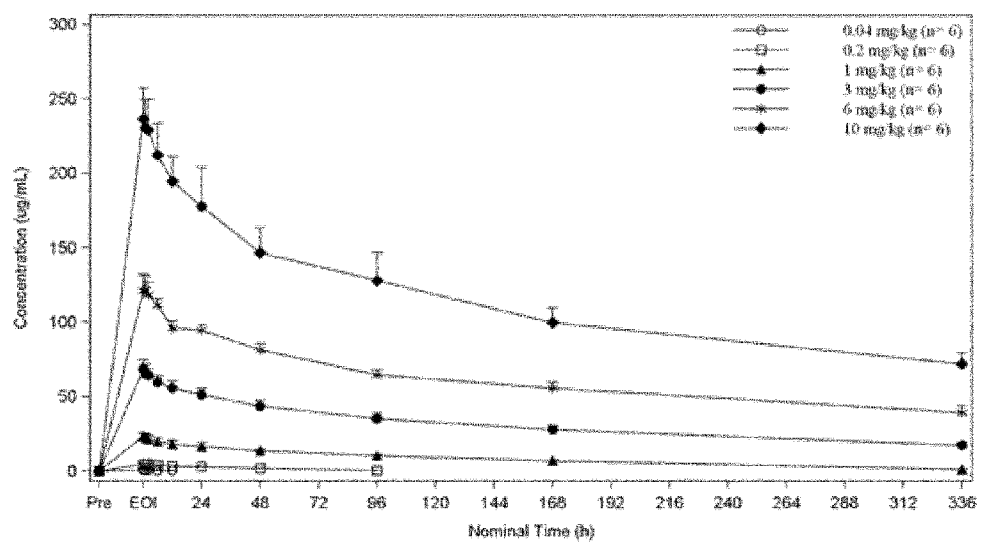

Transition in mean serum concentration of H3-2L4 after single-dose intravenous administration of H3-2L4 to healthy adults (until 8 weeks after administration, linear representation)
    The points in the figure each show a mean value + standard deviation.
    EOI = End of infusion (immediately after completion of single-dose intravenous administration by drip infusion for approximately 30 minutes)
    Nominal time (h) = Time elapsed (h) immediately after completion of administration specified in trial protocol
    Pre = Pre dose (immediately before administration)
    840 h and more after completion of administration to 0.2 mg/kg group, n = 5

[FIG. 2]
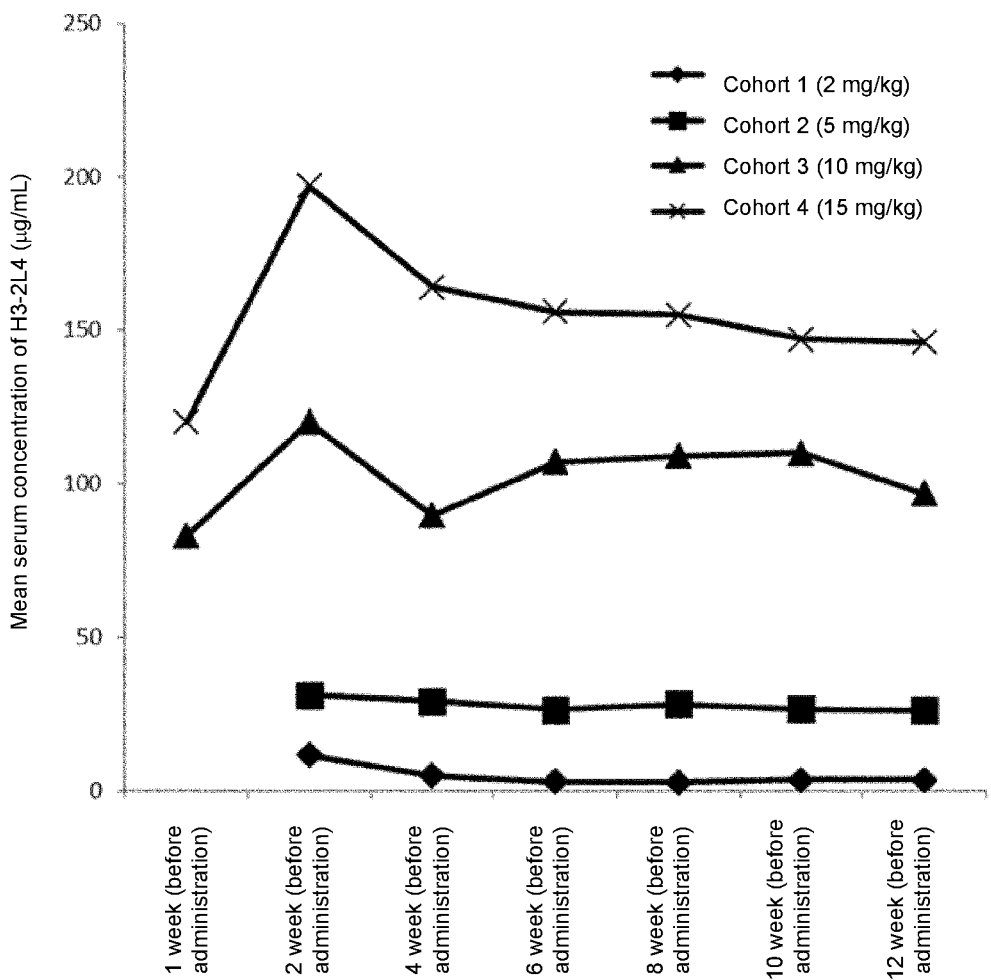

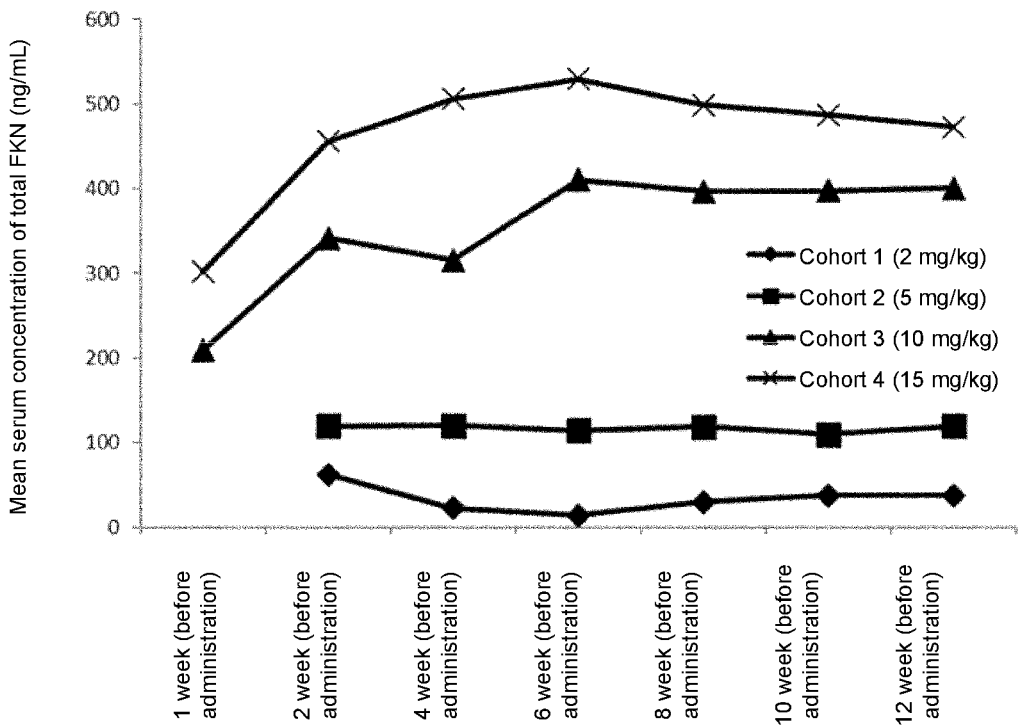
[FIG. 3]

[FIG. 4]
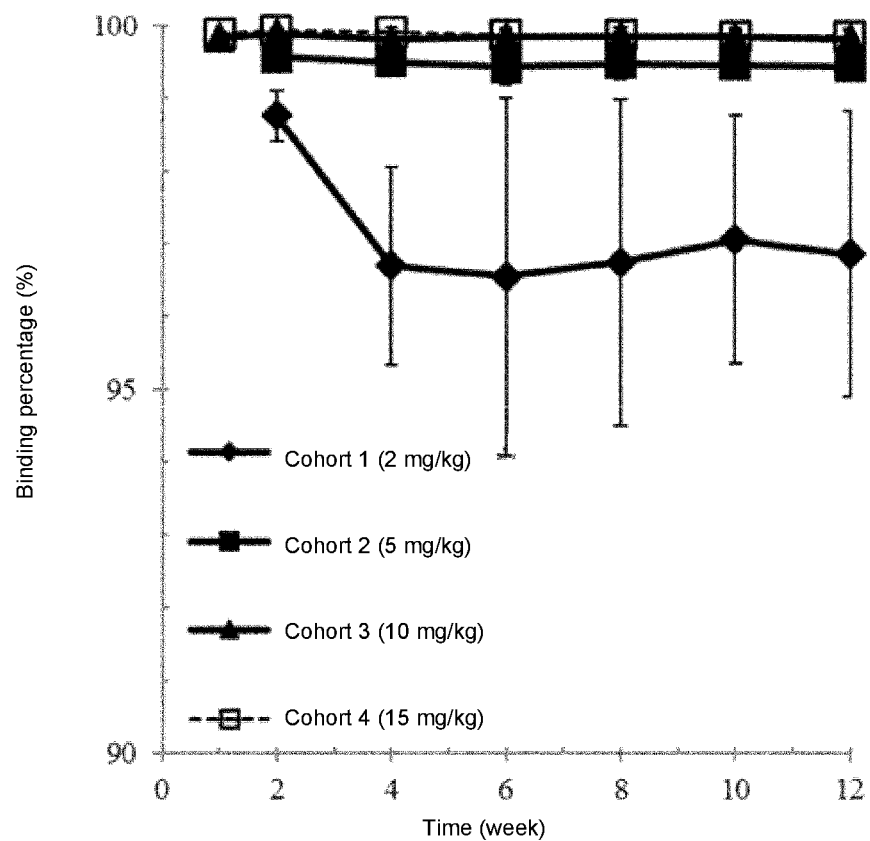
[FIG. 5]
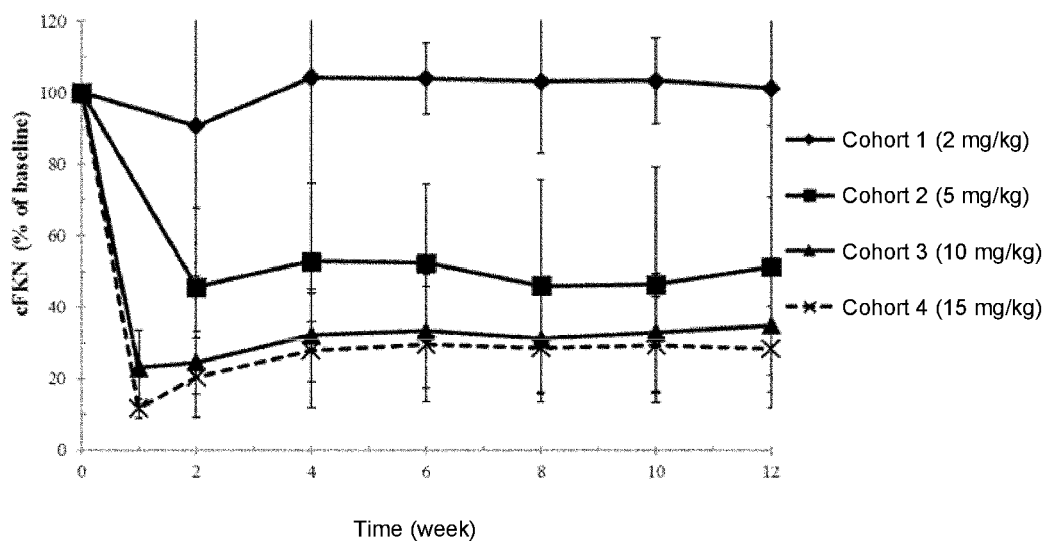

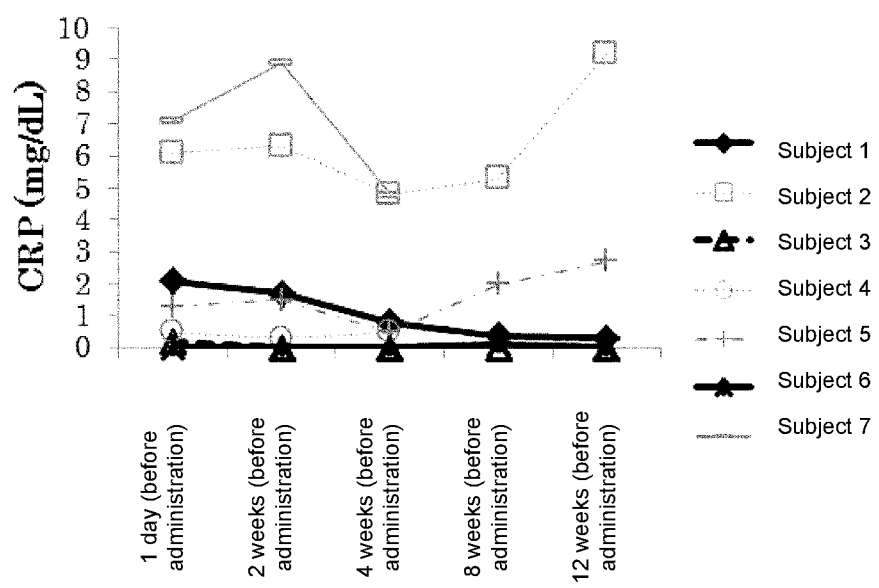
[FIG. 6]

```
                              SEQUENCE LISTING

<160> NUMBER OF SEQ ID NOS: 26

<210> SEQ ID NO 1
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Lys Gln Ala Pro Gly Gln Gly Leu Glu Trp Ile
        35                  40                  45

Gly Trp Ile Tyr Pro Gly Asp Gly Ser Pro Lys Phe Asn Glu Arg Phe
    50                  55                  60

Lys Gly Arg Thr Thr Leu Thr Ala Asp Lys Ser Thr Asn Thr Ala Tyr
65                  70                  75                  80

Met Leu Leu Ser Ser Leu Arg Ser Glu Asp Thr Ala Val Tyr Phe Cys
                85                  90                  95

Ala Thr Gly Pro Thr Asp Gly Asp Tyr Phe Asp Tyr Trp Gly Gln Gly
            100                 105                 110

Thr Thr Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Phe
            20                  25                  30

Leu Ala Trp Tyr Gln Gln Lys Pro Gly Lys Ala Pro Lys Leu Leu Ile
        35                  40                  45

Tyr Asn Glu Lys Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Phe Trp Ser Thr Pro Tyr
                85                  90                  95

Thr Phe Gly Gly Gly Thr Lys Val Glu Ile Lys
            100                 105
```

```
<210> SEQ ID NO 3
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 3

Met Glu Trp Ser Trp Val Phe Leu Phe Phe Leu Ser Val Thr Thr Gly
1               5                   10                  15

Val His Ser

<210> SEQ ID NO 4
<211> LENGTH: 326
<212> TYPE: PRT
<213> ORGANISM: Artificial Sequence
<220> FEATURE:
<223> OTHER INFORMATION: Synthetic polypeptide

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285
```

```
Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 5
<211> LENGTH: 464
<212> TYPE: PRT
<213> ORGANISM: Artificial Sequence
<220> FEATURE:
<223> OTHER INFORMATION: Synthetic polypeptide

<400> SEQUENCE: 5

Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Asn Tyr Tyr Ile His Trp Val Lys Gln Ala Pro Gly Gln Gly Leu
        50                  55                  60

Glu Trp Ile Gly Trp Ile Tyr Pro Gly Asp Gly Ser Pro Lys Phe Asn
65                  70                  75                  80

Glu Arg Phe Lys Gly Arg Thr Thr Leu Thr Ala Asp Lys Ser Thr Asn
                85                  90                  95

Thr Ala Tyr Met Leu Leu Ser Ser Leu Arg Ser Glu Asp Thr Ala Val
            100                 105                 110

Tyr Phe Cys Ala Thr Gly Pro Thr Asp Gly Asp Tyr Phe Asp Tyr Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Ala Ala Ala Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Phe Arg Val Val
305                 310                 315                 320
```

Ser Val Leu Thr Val Val His Gln Asp Trp Leu Asn Gly Lys Glu Tyr
            325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
            355                 360                 365

Pro Pro Ser Arg Glu Glu Met Thr Lys Asn Gln Val Ser Leu Thr Cys
        370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 6
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 6

Met Ser Val Pro Thr Gln Val Leu Gly Leu Leu Leu Leu Trp Leu Thr
1               5                   10                  15

Asp Ala Arg Cys
            20

<210> SEQ ID NO 7
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 7

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 8
<211> LENGTH: 234
<212> TYPE: PRT

<213> ORGANISM: Artificial Sequence
<220> FEATURE:
<223> OTHER INFORMATION: Synthetic polypeptide

<400> SEQUENCE: 8

```
Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gly Asn
        35                  40                  45

Ile His Asn Phe Leu Ala Trp Tyr Gln Gln Lys Pro Gly Lys Ala Pro
    50                  55                  60

Lys Leu Leu Ile Tyr Asn Glu Lys Thr Leu Ala Asp Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Phe Cys Gln Gln Phe Trp
            100                 105                 110

Ser Thr Pro Tyr Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 9
<211> LENGTH: 1417
<212> TYPE: DNA
<213> ORGANISM: Artificial Sequence
<220> FEATURE:
<223> OTHER INFORMATION: Synthetic oligonucleotide

<400> SEQUENCE: 9

```
aagcttgccg ccaccatgga atggtcctgg gtgttcctgt tcttcctgtc cgtgaccacc    60
ggcgtgcact cccaggtgca gctggtgcag tctggcgccg aagtgaagaa acctggcgcc   120
tccgtgaagg tgtcctgcaa ggcctccggc tacaccttca ccaactacta catccactgg   180
gtgaaacagg cccaggaca gggcctggaa tggatcggct ggatctaccc cggcgacggc   240
tcccccaagt tcaacgagcg gttcaagggc cggaccaccc tgaccgccga caagtccacc   300
aacaccgcct acatgctgct gtcctccctg cggagcgagg ataccgccgt gtacttctgc   360
gccaccggcc ctaccgacgg cgactacttc gactactggg gccagggcac caccgtgacc   420
gtgtcctctg cctccaccaa gggcccctcc gtgttcccct ggccccttg ctccggtcc   480 acctctgagt ctaccgccgc tctgggctgc ctggtcaaag actacttccc cgagcctgtg   540
```

| | |
|---|---|
| acagtgtcct ggaactctgg cgccctgacc tctggagtgc ataccttccc tgccgtgctg | 600 |
| cagtcatccg gcctgtactc cctgtcctcc gtggtgacag tgccctcctc caacttcggc | 660 |
| acccagacct acacctgtaa cgtggaccac aagccctcca acaccaaggt ggacaagacc | 720 |
| gtggaacgga agtgctgcgt ggaatgcccc cctgtcctg ccctcctgc cgccgctcct | 780 |
| tccgtgtttc tgttcccccc aaagcccaag gacaccctga tgatctcccg gaccccgaa | 840 |
| gtgacctgcg tggtggtgga cgtgtcccac gaggacccg aggtgcagtt caattggtac | 900 |
| gtggacggcg tggaagtgca acgccaag accaagccca gagaggaaca gttcaactcc | 960 |
| accttccggg tggtgtccgt gctgaccgtg gtgcaccagg actggctgaa cggcaaagag | 1020 |
| tacaagtgca aggtctccaa caagggcctg cctgccccca tcgaaaagac catcagcaag | 1080 |
| accaagggcc agccccgcga gccccaggtg tacacactgc cccccagccg ggaagagatg | 1140 |
| accaagaacc aggtgtccct gacctgtctg gtgaaaggct tctacccctc cgatatcgcc | 1200 |
| gtggaatggg agtccaacgg acagcccgag aacaactaca agaccacccc ccccatgctg | 1260 |
| gactccgacg gctcattctt cctgtactcc aagctgacag tggacaagtc ccggtggcag | 1320 |
| cagggcaacg tgttctcctg cagcgtgatg cacgaggccc tgcacaacca ctacacccag | 1380 |
| aagtccctga gcctgagccc cggcaagtga tgaattc | 1417 |

<210> SEQ ID NO 10
<211> LENGTH: 727
<212> TYPE: DNA
<213> ORGANISM: Artificial Sequence
<220> FEATURE:
<223> OTHER INFORMATION: Synthetic oligonucleotide

<400> SEQUENCE: 10

| | |
|---|---|
| aagcttgccg ccaccatgtc cgtgcccacc caggtgctgg gcctgctgct gctgtggctg | 60 |
| accgacgcca gatgcgacat ccagatgacc cagtcccct ccagcctgtc cgcctctgtg | 120 |
| ggcgacagag tgaccatcac ctgtcgggcc tccggcaaca tccacaactt tctggcctgg | 180 |
| tatcagcaga agcccggcaa ggcccccaag ctgctgatct acaacgaaaa gaccctggcc | 240 |
| gacggcgtgc cctccagatt ctccggctct ggctccggca ccgactacac cctgaccatc | 300 |
| tccagcctgc agcccgagga cttcgccacc tacttttgcc agcagttctg gtccaccccc | 360 |
| tacaccttcg gcggaggcac caaggtggaa atcaagcgga ccgtggccgc tcccccgtg | 420 |
| ttcatcttcc caccctccga cgagcagctg aagtccggca ccgcctccgt ggtgtgcctg | 480 |
| ctgaacaact tctaccccccg cgaggccaag gtgcagtgga aggtggacaa cgccctgcag | 540 |
| tccggcaact cccaggaatc cgtcaccgag caggactcca aggacagcac ctactccctg | 600 |
| tcctccaccc tgaccctgtc caaggccgac tacgagaagc acaaggtgta cgcctgcgaa | 660 |
| gtgacccacc agggcctgtc cagccccgtg accaagtcct caaccgggg cgagtgctga | 720 |
| tgaattc | 727 |

<210> SEQ ID NO 11
<211> LENGTH: 445
<212> TYPE: PRT
<213> ORGANISM: Artificial Sequence
<220> FEATURE:
<223> OTHER INFORMATION: Synthetic polypeptide

<400> SEQUENCE: 11

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Asn Tyr
            20                  25                  30

Tyr Ile His Trp Val Lys Gln Ala Pro Gly Gln Gly Leu Glu Trp Ile
            35                  40                  45

Gly Trp Ile Tyr Pro Gly Asp Gly Ser Pro Lys Phe Asn Glu Arg Phe
50                  55                  60

Lys Gly Arg Thr Thr Leu Thr Ala Asp Lys Ser Thr Asn Thr Ala Tyr
65                  70                  75                  80

Met Leu Leu Ser Ser Leu Arg Ser Glu Asp Thr Ala Val Tyr Phe Cys
                85                  90                  95

Ala Thr Gly Pro Thr Asp Gly Asp Tyr Phe Asp Tyr Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Arg Lys Cys Cys Val Glu
210                 215                 220

Cys Pro Pro Cys Pro Ala Pro Pro Ala Ala Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
```

<210> SEQ ID NO 12
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 12

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Phe
            20                  25                  30

Leu Ala Trp Tyr Gln Gln Lys Pro Gly Lys Ala Pro Lys Leu Leu Ile
        35                  40                  45

Tyr Asn Glu Lys Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Phe Trp Ser Thr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 13
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 13

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Lys Gln Ala Pro Gly Gln Gly Leu Glu Trp Ile
        35                  40                  45

Gly Trp Ile Tyr Pro Gly Asp Gly Ser Pro Lys Phe Asn Glu Arg Phe
    50                  55                  60

Lys Gly Arg Thr Thr Leu Thr Ala Asp Lys Ser Thr Asn Thr Ala Tyr
65                  70                  75                  80
```

```
Met Leu Leu Ser Ser Leu Arg Ser Glu Asp Thr Ala Val Tyr Phe Cys
                 85                  90                  95

Ala Thr Gly Pro Thr Asp Gly Asp Tyr Phe Asp Tyr Trp Gly Gln Gly
            100                 105                 110

Thr Thr Val Thr Val Ser Ser
        115

<210> SEQ ID NO 14
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Phe
            20                  25                  30

Leu Ala Trp Tyr Gln Gln Lys Pro Gly Lys Ala Pro Lys Leu Leu Ile
        35                  40                  45

Tyr Asn Glu Lys Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Phe Trp Ser Thr Pro Tyr
                85                  90                  95

Thr Phe Gly Gly Gly Thr Lys Val Glu Ile Lys
            100                 105

<210> SEQ ID NO 15
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 15

Asn Tyr Tyr Ile His
1               5

<210> SEQ ID NO 16
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 16

Trp Ile Tyr Pro Gly Asp Gly Ser Pro Lys Phe Asn Glu Arg Phe Lys
1               5                   10                  15

Gly

<210> SEQ ID NO 17
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 17

Gly Pro Thr Asp Gly Asp Tyr Phe Asp Tyr
```

```
1               5                   10
```

<210> SEQ ID NO 18
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 18

```
Arg Ala Ser Gly Asn Ile His Asn Phe Leu Ala
1               5                   10
```

<210> SEQ ID NO 19
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 19

```
Asn Glu Lys Thr Leu Ala Asp
1               5
```

<210> SEQ ID NO 20
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 20

```
Gln Gln Phe Trp Ser Thr Pro Tyr Thr
1               5
```

<210> SEQ ID NO 21
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 21

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Lys Gln Ala Pro Gly Gln Gly Leu Glu Trp Ile
        35                  40                  45

Gly Trp Ile Tyr Pro Gly Asp Gly Ser Pro Lys Phe Asn Glu Arg Phe
    50                  55                  60

Lys Gly Arg Thr Thr Leu Thr Ala Asp Lys Ser Thr Asn Thr Ala Tyr
65                  70                  75                  80

Met Leu Leu Ser Ser Leu Arg Ser Asp Asp Thr Ala Val Tyr Phe Cys
                85                  90                  95

Ala Thr Gly Pro Thr Asp Gly Asp Tyr Phe Asp Tyr Trp Gly Gln Gly
            100                 105                 110

Thr Thr Val Thr Val Ser Ser
        115
```

<210> SEQ ID NO 22
<211> LENGTH: 119
<212> TYPE: PRT

<213> ORGANISM: Artificial Sequence
<220> FEATURE:
<223> OTHER INFORMATION: Synthetic polypeptide

<400> SEQUENCE: 22

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
            20                  25                  30
Tyr Ile His Trp Val Arg Gln Ala Pro Gly Gln Gly Leu Glu Trp Ile
        35                  40                  45
Gly Trp Ile Tyr Pro Gly Asp Gly Ser Pro Lys Phe Asn Glu Arg Phe
    50                  55                  60
Lys Gly Arg Thr Thr Leu Thr Arg Asp Lys Ser Thr Asn Thr Ala Tyr
65                  70                  75                  80
Met Glu Leu Ser Ser Leu Arg Ser Asp Asp Thr Ala Val Tyr Phe Cys
                85                  90                  95
Ala Thr Gly Pro Thr Asp Gly Asp Tyr Phe Asp Tyr Trp Gly Gln Gly
            100                 105                 110
Thr Thr Val Thr Val Ser Ser
        115

<210> SEQ ID NO 23
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 23

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
            20                  25                  30
Tyr Ile His Trp Val Arg Gln Ala Pro Gly Gln Gly Leu Glu Trp Ile
        35                  40                  45
Gly Trp Ile Tyr Pro Gly Asp Gly Ser Pro Lys Phe Asn Glu Arg Phe
    50                  55                  60
Lys Gly Arg Thr Thr Met Thr Ala Asp Thr Ser Thr Ser Thr Ala Tyr
65                  70                  75                  80
Met Glu Leu Ser Ser Leu Arg Ser Glu Asp Thr Ala Val Tyr Phe Cys
                85                  90                  95
Ala Arg Gly Pro Thr Asp Gly Asp Tyr Phe Asp Tyr Trp Gly Gln Gly
            100                 105                 110
Thr Thr Val Thr Val Ser Ser
        115

<210> SEQ ID NO 24
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 24

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
            20                  25                  30

```
Tyr Ile His Trp Val Arg Gln Ala Pro Gly Gln Gly Leu Glu Trp Ile
            35                  40                  45

Gly Trp Ile Tyr Pro Gly Asp Gly Ser Pro Lys Phe Asn Glu Arg Phe
 50                  55                  60

Lys Gly Arg Thr Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Gly Pro Thr Asp Gly Asp Tyr Phe Asp Tyr Trp Gly Gln Gly
                100                 105                 110

Thr Thr Val Thr Val Ser Ser
            115

<210> SEQ ID NO 25
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 25

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gly Asn Ile His Asn Phe
            20                  25                  30

Leu Ala Trp Tyr Gln Gln Lys Pro Gly Lys Ala Pro Lys Phe Leu Val
            35                  40                  45

Tyr Asn Glu Lys Thr Leu Ala Asp Gly Val Pro Ser Arg Phe Ser Gly
 50                  55                  60

Ser Gly Ser Gly Thr Gln Tyr Thr Leu Thr Ile Ser Ser Leu Gln Pro
 65                  70                  75                  80

Glu Asp Phe Ala Thr Tyr Phe Cys Gln Gln Phe Trp Ser Thr Pro Tyr
                 85                  90                  95

Thr Phe Gly Gly Gly Thr Lys Val Glu Ile Lys
                100                 105

<210> SEQ ID NO 26
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 26

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gly Asn Ile His Asn Phe
            20                  25                  30

Leu Ala Trp Tyr Gln Gln Lys Pro Gly Lys Ala Pro Lys Leu Leu Ile
            35                  40                  45

Tyr Asn Glu Lys Thr Leu Ala Asp Gly Val Pro Ser Arg Phe Ser Gly
 50                  55                  60

Ser Gly Ser Gly Thr Gln Tyr Thr Leu Thr Ile Ser Ser Leu Gln Pro
 65                  70                  75                  80
```

```
Glu Asp Phe Ala Thr Tyr Phe Cys Gln Gln Phe Trp Ser Thr Pro Tyr
            85                  90                  95
Thr Phe Gly Gly Gly Thr Lys Val Glu Ile Lys
            100             105
```

METHOD AND PHARMACEUTICAL COMPOSITION FOR TREATING CROHN'S DISEASE

FIELD OF THE INVENTION

A part of the content of the present application has been published within 1 year retroactively from the effective filing date of the present application (Apr. 14, 2017) by the inventor of the present application or a joint inventor thereof, or by a third party who had directly learned the subject matter of the present invention from the inventor of the present application at the request of the applicant of the present application, respectively, in the following URL (http://www.gastrojournal.org/article/S0016-5085(16) 32732-9/pdf) (Publication date: Apr. 16, 2016), Gastroenterology (2016), Vol. 150, Issue 4, Supplement 1, Page S808 (Date of issue: Apr. 19, 2016), Digestive Disease Week 2016 Mobile Application (Publication date: on and after Apr. 22, 2016), and in the following URL (https://ddw.scientific-posters.com/epsAbstractDDW.cfm?id=1) (Publication date: May 21, 2016), and Digestive Disease Week 2016 (Publication date: May 23, 2016).

Moreover, another part of the content of the present application has been published within 1 year retroactively from the filing date of the present application by the inventor of the present application or a joint inventor thereof, or by a third party who had directly learned the subject matter of the present invention from the inventor of the present application at the request of the applicant of the present application, respectively, in the following URL (https://www.ecco-ibd.eu/publications/congress-abstract-s/abstracts-2018/item/dop056-efficacy-and-safety-of-anti-fractalkine-monoclonal-antibody-e6011-in-patients-with-crohn-x2019-s-disease-who-had-lost-response-to-anti-tnf-x03b1-agents-a-multicentre-open-label-phase-1-2-study.html) (Publication date: on and after Dec. 1, 2017), ECCO IBD Mobile Application (Publication date: on and after Dec. 1, 2017), and in the following URL (https://academic.oup.com/ecco-jcc/article/12/supplement 1/S070/4808133) (Publication date: Jan. 16, 2018), Journal of Crohn's and Colitis (2018), Vol. 12, Issue supplement 1, Page 5070 (Date of Issue: Jan. 16, 2018), and European Crohn's and Colitis Organisation 2018 (Publication date: Feb. 16, 2018).

The present invention relates to a pharmaceutical composition for treating Crohn's disease, comprising an anti-fractalkine antibody, and a method for treating Crohn's disease.

DESCRIPTION OF THE RELATED ART

Fractalkine (which is also referred to as "FKN") is a membrane-bound chemokine that is expressed on the surface of a vascular endothelial cell by inflammatory stimulation of LPS, TNF-α, IL-1 or the like. Cells that express an FKN receptor, CX3CR1, bind to the membrane-bound FKN without mediation of selectin or integrin, and cause strong cell adhesion. In addition, secretory FKN shedding from the membrane-bound FKN exhibits a cell migration activity on NK cells, T cells and monocytes having CX3CR1.

The expression of FKN is induced by proinflammatory cytokine on the surface of a vascular endothelial cell. It has been reported that an increase in the expression of FKN and accumulation of $CX3CR1^+$ cytotoxic effector lymphocytes and macrophages are observed in patients having Crohn's disease (which is also referred to as "CD").

To date, FKN has been considered to be a promising therapeutic target to ulcerative colitis (which is also referred to as "UC") and inflammatory bowel disease (which is also referred to as "IBD") such as CD (Ann. NY Acad. Sci. 2009; 1173: 350-356). Moreover, it has been suggested that an anti-fractalkine antibody that inhibits the interaction of FKN with CX3CR1 be able to treat IBD including Crohn's disease (WO2006/046739). Thus, it has been suggested that an antibody capable of binding to FKN and inhibiting the action of the FKN be effective for the treatment of Crohn's disease.

To date, the present applicant has reported a plurality of mouse anti-human fractalkine (hFKN) monoclonal antibodies (clones 1F3-1, 3A5-2, 1F3, 1G1, 2B2, 3D5, 3H7, 6D1, 7F6, and 5H7-6). In particular, since the clone 3A5-2 has high neutralizing activity, binding affinity and interspecies cross-reactivity to hFKN, it has been humanized and named as "H3-2L4" (WO2011/052799, which is incorporated herein by reference in its entirety).

It is an object of the present invention to provide a pharmaceutical composition comprising an anti-fractalkine antibody (which is also referred to as an "anti-FKN antibody" in the present description) that provides therapeutically effective improvement to Crohn's disease, after it has been administered to a human subject.

It is another object of the present invention to provide a pharmaceutical composition comprising an anti-FKN antibody, which is used to provide therapeutically effective improvement to Crohn's disease.

It is a further object of the present invention to provide a method for treating Crohn's disease, which provides therapeutically effective improvement to Crohn's disease.

SUMMARY OF THE INVENTION

The present invention includes the following embodiments.
[1] A method for treating Crohn's disease, comprising intravenously administering to a human in need thereof, an anti-fractalkine antibody at a dose of at least 10 mg/kg of human body weight, wherein
  the anti-fractalkine antibody is an antibody comprising:
    a heavy chain variable region comprising the amino acid sequence shown in SEQ ID NO: 13

(QVQLVQSGAEVKKPGASVKVSCKASGYTFTNYYIHWVKQAPGQGLEWIGW

IYPGDGSPKFNERFKGRTTLTADKSTNTAYMLLSSLRSEDTAVYFCATGPT

DGDYFDYWGQGTTVTVSS);

a light chain variable region comprising the amino acid sequence shown in SEQ ID NO: 14

(DIQMTQSPSSLSASVGDRVTITCRASGNIHNFLAWYQQKPGKAPKLLIYN

EKTLADGVPSRFSGSGSGTDYILTISSLQPEDFATYFCQQFWSTPYTFGGG

TKVEIK);

and
  a constant region of human IgG2 isotype, wherein
    the Fc region of the constant region of human IgG2 isotype comprises mutations V234A and G237A.
[2] The method according to the above [1], wherein
  the anti-fractalkine antibody is intravenously administered to a human at a dose of 10 to 15 mg/kg of human body weight.

[3] The method according to the above [1], wherein
the anti-fractalkine antibody is intravenously administered to a human in need thereof at a dose of 10 mg/kg of human body weight or 15 mg/kg of human body weight.

[4] The method according to the above [1], characterized by intravenously administrating a pharmaceutical composition, which is formulated, such that it provides a mean $C_{max}$ of the anti-fractalkine antibody at a dose of 1 mg/kg of human body weight that is a value of 21 to 25 µg/mL.

[5] The method according to the above [1], characterized by intravenously administrating a pharmaceutical composition, which is formulated, such that when the anti-fractalkine antibody is administered to a human by single-dose intravenous administration at a dose of 10 mg/kg of human body weight, it provides a mean $C_{max}$ of the anti-fractalkine antibody that is a value included in the numerical range of 80% to 125% of $2.4 \times 10^2$ µg/mL.

[6] The method according to the above [1], characterized by intravenously administrating a pharmaceutical composition, which is formulated, such that when the anti-fractalkine antibody is administered to a human by single-dose intravenous administration at a dose of 10 mg/kg of human body weight, it provides a mean $AUC_{(0-t)}$ of the anti-fractalkine antibody that is a value included in the numerical range of 80% to 125% of $7.0 \times 10^4$ µg·h/mL.

[7] The method according to the above [1], characterized by intravenously administrating a pharmaceutical composition, which is formulated, such that when the anti-fractalkine antibody is administered to a human by single-dose intravenous administration at a dose of 10 mg/kg of human body weight, it provides a mean $AUC_{(0-336h)}$ of the anti-fractalkine antibody that is a value included in the numerical range of 80% to 125% of $3.8 \times 10^4$ µg·h/mL.

[8] The method according to the above [1], which comprises multiple-dose intravenous administration of the anti-fractalkine antibody at dosing intervals from once every week to once every two weeks.

[9] The method according to any one of the above [1] to [8], which comprises intravenous administration of the anti-fractalkine antibody, such that the mean trough concentration of the anti-fractalkine antibody is 80 µg/mL or more.

Moreover, in another aspect, the present invention relates to the following inventions.

[1'] A pharmaceutical composition for treating Crohn's disease, which comprises an anti-fractalkine antibody and a pharmaceutically acceptable excipient, wherein
the anti-fractalkine antibody is an antibody comprising:
a heavy chain variable region comprising the amino acid sequence shown in SEQ ID NO: 13

(QVQLVQSGAEVKKPGASVKVSCKASGYTFTNYYIHWVKQAPGQGLEWIGW

IYPGDGSPKFNERFKGRTTLTADKSTNTAYMLLSSLRSEDTAVYFCATGPT

DGDYFDYWGQGTTVTVSS);

a light chain variable region comprising the amino acid sequence shown in SEQ ID NO: 14

(DIQMTQSPSSLSASVGDRVTITCRASGNIHNFLAWYQQKPGKAPKLLIYN

EKTLADGVPSRFSGSGSGTDYILTISSLQPEDFATYFCQQFWSTPYTFGGG

TKVEIK);

and
a constant region of human IgG2 isotype, wherein
the Fc region of the constant region of human IgG2 isotype comprises mutations V234A and G237A, and
the pharmaceutical composition is used, such that the anti-fractalkine antibody is intravenously administered to a human at a dose of at least 10 mg/kg of human body weight.

[2'] The pharmaceutical composition according to the above [1'], which is used, such that
the anti-fractalkine antibody is intravenously administered to a human at a dose of 10 to 15 mg/kg of human body weight.

[3'] The pharmaceutical composition according to the above [1'], which is used, such that the anti-fractalkine antibody is intravenously administered to a human at a dose of 10 mg/kg of human body weight or 15 mg/kg of human body weight.

[4'] The pharmaceutical composition according to the above [1'], wherein
when the pharmaceutical composition is administered to a human by single-dose intravenous administration, the mean $C_{max}$ of the anti-fractalkine antibody at a dose of 1 mg/kg of human body weight is 21 to 25 µg/mL.

[5'] The pharmaceutical composition according to the above [1'], wherein
when the anti-fractalkine antibody is administered to a human by single-dose intravenous administration at a dose of 10 mg/kg of human body weight, the mean $C_{max}$ of the anti-fractalkine antibody is a value included in the numerical range of 80% to 125% of $2.4 \times 10^2$ µg/mL.

[6'] The pharmaceutical composition according to the above [1'], wherein
when administered to a human by single-dose intravenous administration at a dose of 10 mg/kg of human body weight, the mean $AUC_{(0-t)}$ of the anti-fractalkine antibody is a value included in the numerical range of 80% to 125% of $7.0 \times 10^4$ µg·h/mL.

[7'] The pharmaceutical composition according to the above [1'], wherein
when the anti-fractalkine antibody is administered to a human by single-dose intravenous administration at a dose of 10 mg/kg of human body weight, the mean $AUC_{(0-336h)}$ of the anti-fractalkine antibody is a value included in the numerical range of 80% to 125% of $3.8 \times 10^4$ µg·h/mL.

[8'] The pharmaceutical composition according to the above [1'], which is administered by multiple-dose intravenous administration at dosing intervals from once every week to once every two weeks.

[9'] The pharmaceutical composition according to any one of the above [1'] to [7'], which is intravenously administered, such that the mean trough concentration of the anti-fractalkine antibody is 80 µg/mL or more.

[10'] A pharmaceutical composition for use in a method for treating Crohn's disease, wherein
the pharmaceutical composition comprises an anti-fractalkine antibody and a pharmaceutically acceptable excipient, and
the therapeutic method comprises intravenously administering a therapeutically effective amount of the anti-fractalkine antibody to a human in need thereof, wherein
the anti-fractalkine antibody is an antibody comprising:
a heavy chain variable region comprising the amino acid sequence shown in SEQ ID NO: 13

(QVQLVQSGAEVKKPGASVKVSCKASGYTFTNYYIHWVKQAPGQGLEWIGW

IYPGDGSPKFNERFKGRTTLTADKSTNTAYMLLSSLRSEDTAVYFCATGPT

DGDYFDYWGQGTTVTVSS);

a light chain variable region comprising the amino acid sequence shown in SEQ ID NO: 14

(DIQMTQSPSSLSASVGDRVTITCRASGNIHNFLAWYQQKPGKAPKLLIYN EKTLADGVPSRFSGSGSGTDYILTISSLQPEDFATYFCQQFWSTPYTFGGG TKVEIK);

and a constant region of human IgG2 isotype, wherein the Fc region of the constant region of human IgG2 isotype comprises mutations V234A and G237A, wherein the therapeutically effective amount is a dose, which provides any one, or two, or three of the following pharmacokinetic parameters when the therapeutically effective amount of the anti-fractalkine antibody is administered by single-dose intravenous administration of the pharmaceutical composition comprising the anti-fractalkine antibody:

the mean $C_{max}$ of the anti-fractalkine antibody is a value included in the numerical range of 80% to 125% of $2.4 \times 10^2$ μg/mL;

the mean $AUC_{(0-t)}$ of the anti-fractalkine antibody is a value included in the numerical range of 80% to 125% of $7.0 \times 10^4$ μg·h/mL; and the mean $AUC_{(0-336h)}$ of the anti-fractalkine antibody is a value included in the numerical range of 80% to 125% of $3.8 \times 10^4$ μg·h/mL.

Inventions comprising any given combination of one or more of the above-mentioned aspects of the present invention are also included in the scope of the present invention.

According to the present invention, there is provided a pharmaceutical composition comprising an anti-FKN antibody that provides therapeutically effective improvement to Crohn's disease, after it has been administered to a human subject. The pharmaceutical composition of the present invention can be used to provide the pharmacokinetic parameters of the anti-FKN antibody useful for exhibiting therapeutic effects on Crohn's disease.

According to the present invention, there is also provided a method of treating Crohn's disease, which provides therapeutically effective improvement to Crohn's disease.

BRIEF DESCRIPTION OF THE DRAWINGS

FIG. 1 shows the mean serum concentration of H3-2L4 over time, after single-dose intravenous administration of the antibody H3-2L4 (0.04 mg/kg, 0.2 mg/kg, 1 mg/kg, 3 mg/kg, 6 mg/kg and 10 mg/kg administration groups);

FIG. 2 shows the mean serum concentration of H3-2L4 over time, after multiple-dose intravenous administration of the antibody H3-2L4 (2 mg/kg, 5 mg/kg, 10 mg/kg and 15 mg/kg administration groups);

FIG. 3 shows the mean serum concentration of total FKN over time, upon multiple-dose intravenous administration of the antibody H3-2L4 (2 mg/kg, 5 mg/kg, 10 mg/kg and 15 mg/kg administration groups);

FIG. 4 shows the binding occupancy of the antibody H3-2L4 to mFKN over time, based on simulation using QSS models;

FIG. 5 shows the percentage of the cFKN amount to the cFKN amount before initiation of the administration over time, based on simulation using QSS models; and FIG. 6 shows the CRP of seven subjects in Cohort 3 (10 mg/kg group) over time, until 12 weeks after administration.

DETAILED DESCRIPTION OF THE PREFERRED EMBODIMENTS

1. Outline and Definition of the Invention

The present invention relates to a pharmaceutical composition providing therapeutically effective improvement to Crohn's disease, and a method of treating Crohn's disease.

In one embodiment of the present invention, "therapeutically effective improvement to Crohn's disease" can mean that therapeutically effective improvement is shown in one or more evaluation criteria of Crohn's disease, which have been established in the present technical field. Examples of such evaluation criteria that can be used herein include, but are not limited to, Crohn's disease activity index (also referred to as "CDAI"), The International Organization for the study of Inflammatory Bowel Disease score (also referred to as "IOIBD score"), and Dutch activity index (also referred to as "Dutch-AI"), in which the symptoms of inflammatory bowel disease, such as diarrhea, intestinal pain, common state, parenteral complication, perianal abscess, fistula, fever and weight reduction are shown as activity indexes. In addition, another example of such evaluation criteria is detection of the serum level of C-reactive protein (also referred to as "CRP") in patients. With regard to severity classification according to CDAI, a value of less than 150 indicates remission, a value from 150 to 219 indicates a mild case of disease activity, a value from 220 to 450 indicates a medium case of disease activity, and a value of more than 450 indicates a severe case of disease activity.

In one embodiment of the present invention, when the CDAI score before treatment is 220 or more, and the CDAI score after treatment is reduced by 70 or more, and more preferably by 100 or more, using the CDAI score before treatment as a baseline, or when the CDAI score after treatment is preferably less than 150 (remission), it means that "therapeutically effective improvement is provided to Crohn's disease."

In one aspect, the present invention relates to a pharmaceutical composition for treating Crohn's disease, which provides the therapeutically effective serum concentration of an anti-FKN antibody, after single-dose or multiple-dose administration of the pharmaceutical composition to a human subject. In another aspect, the present invention relates to a method for treating Crohn's disease, comprising administering an anti-FKN antibody to a human subject, such that it provides the therapeutically effective serum concentration of the anti-FKN antibody.

In one embodiment of the present invention, the "therapeutically effective serum concentration of an anti-FKN antibody" is the serum concentration of an anti-FKN antibody that is 20 μg/mL or more, 30 μg/mL or more, 40 μg/mL or more, 50 μg/mL or more, 60 μg/mL or more, 70 μg/mL or more, or 80 μg/mL or more. In addition, in another embodiment of the present invention, the "therapeutically effective serum concentration of an anti-FKN antibody" is the mean trough concentration of an anti-FKN antibody that is 20 μg/mL or more, 30 μg/mL or more, 40 μg/mL or more, 50 μg/mL or more, 60 μg/mL or more, 70 μg/mL or more, or 80 μg/mL or more. In a preferred embodiment, the "therapeutically effective serum concentration of an anti-FKN antibody" is the mean trough concentration of an anti-FKN antibody that is 70 μg/mL or more, or 80 μg/mL or more. In a more preferred embodiment, the "therapeutically effective serum concentration of an anti-FKN antibody" is the mean trough concentration of an anti-FKN antibody that is 80 μg/mL or more.

Accordingly, in one aspect, the anti-FKN antibody of the present invention is formulated and/or administered, such that 20 µg/mL or more, 30 µg/mL or more, 40 µg/mL or more, 50 µg/mL or more, 60 µg/mL or more, 70 µg/mL or more, or 80 µg/mL or more of the serum concentration of the anti-FKN antibody is provided. In a preferred embodiment, the anti-FKN antibody of the present invention is formulated and/or administered, such that 70 µg/mL or more of the serum concentration of the anti-FKN antibody is provided. In another preferred embodiment of the present invention, the anti-FKN antibody of the present invention is formulated and/or administered, such that 80 µg/mL or more of the serum concentration of the anti-FKN antibody is provided.

In another aspect, the present invention relates to a pharmaceutical composition comprising an anti-FKN antibody, which is used to provide the serum concentration of the anti-FKN antibody that is therapeutically effective for a human subject, after single-dose administration or multiple-dose administration of the pharmaceutical composition to the human subject. The form of the pharmaceutical composition of the present invention is not particularly limited, and it can be typically the form of an injection formulation prepared for intravenous administration. In one embodiment, the pharmaceutical composition of the present invention is used, in the therapeutic method of the present invention, such that the mean trough concentration of the anti-FKN antibody is 20 µg/mL or more, 30 µg/mL or more, 40 µg/mL or more, 50 µg/mL or more, 60 µg/mL or more, 70 µg/mL or more, or 80 µg/mL or more. In a preferred embodiment, the pharmaceutical composition of the present invention is used, in the therapeutic method of the present invention, such that the mean trough concentration of the anti-FKN antibody is 70 µg/mL or more, or 80 µg/mL or more.

In the present invention, the pharmacokinetic properties of a concentration-time curve, such as the maximum observed serum concentration ($C_{max}$), the time to reach $C_{max}$ ($T_{max}$), and area under the serum concentration time curve (AUC), are examined by statistical methods sufficiently established in the field of pharmacokinetics. When the ratio between the population mean of the evaluation parameters in a study preparation and the population mean of the evaluation parameters in a standard preparation is 0.80 to 1.25, the two preparations are generally considered to be biologically equivalent to each other.

In the present invention, the mean values of the pharmacokinetic parameters, such as $C_{max}$ or AUC, can be calculated by any one method of the geometric mean, the arithmetical mean, and the median. In the present description, the mean $C_{max}$, the mean AUC, the mean trough concentration, and the mean tFNK concentration are indicated with the arithmetical mean value, unless otherwise specified. Even if the mean value as a target is calculated by a method that is different from the method described in the present description, if the mean value calculated by the method described in the present description is within the numerical range described in the claims, the calculated mean value is intended to belong to the claims according to the present invention.

In the present invention, with regard to the dose of the anti-FKN antibody, "a dose" or "at a dose" means the absolute amount of the anti-FKN antibody for a single administration. Accordingly, when the expression "at a dose of 10 mg/kg of human body weight" is used, for example, it means that the anti-FKN antibody is administered in an amount calculated by multiplying 10 mg by human body weight (kg), by administration of one set of, or simultaneously used two or more sets of, the pharmaceutical composition of the present invention.

In the present invention, with regard to the dosing intervals of the anti-FKN antibody, for example, the expression "dosing intervals from once every week to once every two weeks" means a dosing interval from an $n^{th}$ number of administration (wherein n is an integer) to an $n+1^{th}$ number of administration is from one week to two weeks. The dosing interval from the $n^{th}$ number of administration to the $n+1^{th}$ number of administration may be different from a dosing interval from the $n+1^{th}$ number of administration to an $n+2^{th}$ number of administration. For instance, a case where the dosing interval from the first administration to the second administration is 1 week and the dosing interval from the second administration to the third administration is 2 weeks is naturally included in the "dosing intervals from once every week to once every two weeks."

In the present description, the term "human" or "human subject" is used to mean a healthy adult male, and typically, any given human who exhibits Crohn's disease, or the clinical signs and symptoms of any given disease or disorder, which may develop Crohn's disease. In the present invention, the "human" or the "human subject" is preferably a Crohn's disease patient who has not been obtained sufficient therapeutic effects from at least one time of the standard of care (corticosteroid, an immunomodulator and/or an anti-TNF antibody), or who has not had continuous therapeutic effects therefrom, or who has been intolerant thereto.

2. Anti-FKN Antibody

In the present invention, when an anti-FKN antibody is referred to, the anti-FKN antibody means the humanized anti-human fractalkine antibody H3-2L4, or an antibody functionally equivalent thereto. In the present invention, the "functionally equivalent antibody" means an antibody equivalent to the antibody H3-2L4, in terms of at least any one, or preferably two or more of binding affinity to human FKN, neutralizing activity, cross-reactivity, and blood pharmacokinetics.

In the present invention, when an anti-FKN antibody is referred to, the anti-FKN antibody may include an antigen-binding fragment thereof. Such an antigen-binding fragment is not particularly limited, as long as it is a functional and structural fragment of the anti-FKN antibody, which retains bindability to FKN and is not significantly different from a complete antibody thereof in terms of blood pharmacokinetics. Examples of such an antigen-binding fragment of an antibody include, but are not limited to, Fab, Fab', F(ab')$_2$, Fv, single-stranded Fv (ScFv), their variants, and other modification structures, such as a fusion protein comprising an antibody portion and an immunoglobulin molecule containing an antigen recognition site.

In one embodiment, the anti-FKN antibody of the present invention may be any given antibody comprising the following CDR sequences:
 (a) CDR-H1 comprising the amino acid sequence shown in SEQ ID NO: 15 (NYYIH);
 (b) CDR-H2 comprising the amino acid sequence shown in SEQ ID NO: 16 (WIYPGDGSPKFNERFKG);
 (c) CDR-H3 comprising the amino acid sequence shown in SEQ ID NO: 17 (GPTDGDYFDY);
 (d) CDR-L1 comprising the amino acid sequence shown in SEQ ID NO: 18 (RASGNIHNFLA);
 (e) CDR-L2 comprising the amino acid sequence shown in SEQ ID NO: 19 (NEKTLAD); and (f) CDR-L3 comprising the amino acid sequence shown in SEQ ID NO: 20 (QQFWSTPYT).

In another embodiment, the anti-FKN antibody may be an antibody comprising a heavy chain and a light chain, wherein the heavy chain variable region of the antibody comprises the amino acid sequence shown in SEQ ID NO: 21

SEQ ID NO: 21
(QVQLVQSGAEVKKPGASVKVSCKASGYTFTNYYTHWVKQAPGQGLEWIGW
IYPGDGSPKFNERFKGRTTLTADKSTNTAYMLLSSLRSDDTAVYFCATGPT
DGDYFDYWGQGTTVTVSS),

SEQ ID NO: 13
(QVQLVQSGAEVKKPGASVKVSCKASGYTFTNYYTHWVKQAPGQGLEWIGW
IYPGDGSPKFNERFKGRTTLTADKSTNTAYMLLSSLRSEDTAVYFCATGPT
DGDYFDYWGQGTTVTVSS),

SEQ ID NO: 22
(QVQLVQSGAEVKKPGASVKVSCKASGYTFTNYYTHWVRQAPGQGLEWIGW
IYPGDGSPKFNERFKGRTTLTRDKSTNTAYMELSSLRSDDTAVYFCATGPT
DGDYFDYWGQGTTVTVSS),

SEQ ID NO: 23
(QVQLVQSGAEVKKPGASVKVSCKASGYTFTNYYTHWVRQAPGQGLEWIGW
IYPGDGSPKFNERFKGRTTMTADTSTSTAYMELSSLRSEDTAVYFCARGPT
DGDYFDYWGQGTTVTVSS),
or

SEQ ID NO: 24
(QVQLVQSGAEVKKPGASVKVSCKASGYTFTNYYTHWVRQAPGQGLEWIGW
IYPGDGSPKFNERFKGRTTLTADKSTSTAYMELSSLRSEDTAVYFCARGPT
DGDYFDYWGQGTTVTVSS), and the light chain variable region of the antibody comprises the amino acid sequence shown in SEQ ID NO: 25
(DIQMTQSPSSLSASVGDRVTITCRASGNIHNFLAWYQQKPGKAPKFLVYN
EKTLADGVPSRFSGSGSGTQYTLTISSLQPEDFATYFCQQFWSTPYTFGGG
TKVEIK), SEQ ID NO: 14
(DIQMTQSPSSLSASVGDRVTITCRASGNIHNFLAWYQQKPGKAPKLLIYN
EKTLADGVPSRFSGSGSGTDYTLTISSLQPEDFATYFCQQFWSTPYTFGGG
TKVEIK),
or SEQ ID NO: 26
(DIQMTQSPSSLSASVGDRVTITCRASGNIHNFLAWYQQKPGKAPKLLIYN
EKTLADGVPSRFSGSGSGTQYTLTISSLQPEDFATYFCQQFWSTPYTFGGG
TKVEIK).

In a preferred embodiment, the anti-FKN antibody may be an antibody comprising a heavy chain and a light chain, wherein the heavy chain variable region of the antibody comprises the amino acid sequence shown in SEQ ID NO: 13

(QVQLVQSGAEVKKPGASVKVSCKASGYTFTNYYIHWVKQAPGQGLEWIGW
IYPGDGSPKFNERFKGRTTLTADKSTNTAYMLLSSLRSEDTAVYFCATGPT
DGDYFDYWGQGTTVTVSS), and the light chain variable region of the antibody comprises the amino acid sequence shown in SEQ ID NO: 14

(DIQMTQSPSSLSASVGDRVTITCRASGNIHNFLAWYQQKPGKAPKLLIYN
EKTLADGVPSRFSGSGSGTDYTLTISSLQPEDFATYFCQQFWSTPYTFGGG
TKVEIK).

In a specific embodiment, the anti-FKN antibody is an antibody comprising a constant region of human IgG2 isotype.

In a specific embodiment, the anti-FKN antibody is an antibody wherein the Fc region of the constant region of human IgG2 isotype comprises mutations V234A and/or G237A.

In a particularly preferred embodiment of the present invention, the anti-FKN antibody is the antibody H3-2L4, which consists of a heavy chain consisting of the amino acid sequence shown in SEQ ID NO: 11

(QVQLVQSGAEVKKPGASVKVSCKASGYTFTNYYIHWVKQAPGQGLEWI
GWIYPGDGSPKFNERFKGRTTLTADKSTNTAYMLLSSLRSEDTAVYFCA
TGPTDGDYFDYWGQGTTVTVSSASTKGPSVFPLAPCSRSTSESTAALGC
LVKDYFPEPVTVSWNSGALTSGVHTFPAVLQSSGLYSLSSVVTVPSSNF
GTQTYTCNVDHKPSNTKVDKTVERKCCVECPPCPAPPAAAPSVFLFPPK
PKDTLMISRTPEVTCVVVDVSHEDPEVQFNWYVDGVEVHNAKTKPREEQ
FNSTFRVVSVLTVVHQDWLNGKEYKCKVSNKGLPAPIEKTISKTKGQPR
EPQVYTLPPSREEMTKNQVSLTCLVKGFYPSDIAVEWESNGQPENNYKT
TPPMLDSDGSFFLYSKLTVDKSRWQQGNVFSCSVMHEALHNHYTQKSLS
LSPGK)

and a light chain consisting of the amino acid sequence shown in SEQ ID NO: 12

(DIQMTQSPSSLSASVGDRVTITCRASGNIHNFLAWYQQKPGKAPKLLI
YNEKTLADGVPSRFSGSGSGTDYTLTISSLQPEDFATYFCQQFWSTPYT
FGGGTKVEIKRTVAAPSVFIFPPSDEQLKSGTASVVCLLNNFYPREAKV
QWKVDNALQSGNSQESVTEQDSKDSTYSLSSTLTLSKADYEKHKVYACE
VTHQGLSSPVTKSFNRGEC).

An antibody, which is obtained by appropriately modifying the above-exemplified anti-FKN antibody (e.g., modification of the antibody, or partial substitution, addition or deletion of the amino acid sequence of the antibody), while retaining the function of the antibody, or in order to add or improve the function of the antibody, is also included in the antibody of the present invention. More specifically, an antibody whose lysine (Lys) positioned at the carboxy terminus (C-terminus) of a heavy chain has been deleted by an artificial method such as genetic modification to reduce the heterogeneity of an antibody generated from antibody-producing cells is also included in the scope of the present invention. Moreover, the anti-FKN antibody comprised in the pharmaceutical composition of the present invention does not necessarily have complete homogeneity, and thus, the present anti-FKN antibody includes, for example both an antibody that deletes lysine (Lys) positioned at the carboxy terminus (C-terminus) of a heavy chain thereof, and an antibody that does not delete such lysine, as long as it maintains the functions intended by the pharmaceutical composition of the present invention.

The anti-FKN antibody may be modified, as desired. The anti-FKN antibody may be modified to change (a) the three-dimensional structure of an amino acid sequence in a modified region, for example such as a sheet or helix conformation; (b) the charged or hydrophobic state of a molecule at a target site; or (c) the effect of modification on the maintenance of the volume of a side chain. Otherwise, it may also be a modification, in which such changes are not clearly observed.

Modification of the anti-FKN antibody may be achieved, for example, by substitution, deletion, addition or the like of constitutional amino acid residues.

In the present description, the term "amino acid" is used to have the most broad definition, and thus, examples of the amino acid include not only natural amino acids, such as serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gln), threonine (Thr), cysteine (Cys), methionine (Met), phenylalanine (Phe), tryptophan (Trp), and proline (Pro), but also, unnatural amino acids, such as amino acid variants and derivatives. Taking into consideration such a broad definition of the amino acid, a person skilled in the art could naturally understand that examples of the amino acid mentioned in the present description include: L-amino acid; D-amino acid; chemically modified amino acids, such as amino acid variants and amino acid derivatives; amino acids that cannot be materials for constituting proteins in vivo, such as norleucine, β-alanine and ornithine; and chemically synthesized compounds having the properties of amino acids known to such a skilled person. Examples of the unnatural amino acid include α-methyl amino acids (α-methyl alanine, etc.), D-amino acids (D-aspartic acid, D-glutamic acid, etc.), histidine-like amino acids (2-amino-histidine, β-hydroxy-histidine, homohistidine, α-fluoromethyl-histidine, α-methyl-histidine, etc.), amino acids having redundant methylene on a side chain thereof ("homo" amino acid), and amino acids, the carboxylic acid functional group of which is substituted with a sulfonic acid group (cysteic acid, etc.).

Naturally existing amino acid residues can be classified into the following groups, for example, based on general side chain properties:
(1) hydrophobicity: Met, Ala, Val, Leu, Ile;
(2) neutral hydrophilicity: Cys, Ser, Thr;
(3) acidity: Asp, Glu;
(4) basicity: Asn, Gln, His, Lys, Arg;
(5) residues having influence on chain orientation: Gly, Pro; and
(6) aromaticity: Trp, Tyr, Phe.

Non-conservative substitution of amino acid sequences that constitute the anti-FKN antibody may be carried out by exchanging an amino acid belonging to one of these groups with another amino acid belonging to another group. More conservative substitution may be carried out by exchanging an amino acid belonging to one of these groups with another amino acid belonging to the same group. Likewise, deletion or substitution of an amino acid sequence may be carried out, as appropriate.

3. Pharmaceutical Composition and Formulation

The pharmaceutical composition of the present invention comprises a therapeutically effective amount of the anti-FKN antibody. The amount of the anti-FKN antibody comprised in the pharmaceutical composition of the present invention can be varied depending on the administration route of the pharmaceutical composition of the present invention and the dosing intervals.

In one embodiment of the present invention, the pharmaceutical composition of the present invention can comprise the anti-FKN antibody in an amount from 2 mg/kg of human body weight to 15 mg/kg of human body weight. In a specific embodiment of the present invention, the formulation of the present invention can comprise the anti-FKN antibody in an amount of at least 2 mg/kg of human body weight, at least 5 mg/kg of human body weight, at least 10 mg/kg of human body weight, or at least 15 mg/kg of human body weight. In a further embodiment of the present invention, the formulation of the present invention can comprise the anti-FKN antibody in an amount of 2 mg/kg of human body weight, 5 mg/kg of human body weight, 10 mg/kg of human body weight, or 15 mg/kg of human body weight.

The dosage form of the pharmaceutical composition of the present invention is not particularly limited, and it is typically a formulation prepared for use in intravenous administration (e.g., a formulation for injection). In the case of the pharmaceutical composition of the present invention, the anti-FKN antibody, together with a pharmaceutically acceptable excipient, is added into, for example, water for injection, a normal saline, or a phosphate buffered saline, but are not limited thereto, such that it can be prepared in the form of a formulation for injection. Examples of the pharmaceutically acceptable excipient used in the present invention include, but are not limited to, a stabilizer, a surfactant, and a preservative. Representative excipients used for production of a formulation for injection and the production process thereof are known in the present technical field, and for example, Introduction to Pharmaceutical Dosage Forms, 1985, Ansel, H. C., Lea and Febiger, Philadelphia, Pa.; Remington's Pharmaceutical Sciences 1995, Mack Publ. Co., Easton, Pa. can be referred to. These publications are incorporated herein by reference in their entirety.

In one embodiment of the present invention, the pharmaceutical composition of the present invention is a formulation for intravenous administration, in which when the pharmaceutical composition is administered to a human by single-dose intravenous administration, the mean $C_{max}$ of the anti-fractalkine antibody at a dose of 1 mg/kg of human body weight is 21 to 25 µg/mL.

In another embodiment of the present invention, the pharmaceutical composition of the present invention is a formulation for intravenous administration, in which when the anti-fractalkine antibody is administered to a human by single-dose intravenous administration at a dose of 10 mg/kg of human body weight, the mean $C_{max}$ of the anti-fractalkine antibody is a value included in the numerical range of 80% to 125% of $2.4 \times 10^2$ µg·h/mL.

In another embodiment of the present invention, the pharmaceutical composition of the present invention is a formulation for intravenous administration, in which when the anti-fractalkine antibody is administered to a human by single-dose intravenous administration at a dose of 10 mg/kg of human body weight, the mean $AUC_{(0-t)}$ of the anti-fractalkine antibody is a value included in the numerical range of 80% to 125% of $7.0\times10^4$ μg·h/mL.

In another embodiment of the present invention, the pharmaceutical composition of the present invention is a formulation for intravenous administration, in which when the anti-fractalkine antibody is administered to a human by single-dose intravenous administration at a dose of 10 mg/kg of human body weight, the mean $AUC_{(0-336h)}$ of the anti-fractalkine antibody is a value included in the numerical range of 80% to 125% of $3.8\times10^4$ μg·h/mL.

In another embodiment of the present invention, the pharmaceutical composition of the present invention is a formulation for intravenous administration having at least any two of the following characteristics:

when the pharmaceutical composition is administered to a human by single-dose intravenous administration, the mean $C_{max}$ of the anti-fractalkine antibody at a dose of 1 mg/kg of human body weight is 21 to 25 μg/mL;

when the anti-fractalkine antibody is administered to a human by single-dose intravenous administration at a dose of 10 mg/kg of human body weight, the mean $C_{max}$ of the anti-fractalkine antibody is a value included in the numerical range of 80% to 125% of $2.4\times10^2$ μg·h/mL;

when the anti-fractalkine antibody is administered to a human by single-dose intravenous administration at a dose of 10 mg/kg of human body weight, the mean $AUC_{(0-t)}$ of the anti-fractalkine antibody is a value included in the numerical range of 80% to 125% of $7.0\times10^4$ μg·h/mL; and when the anti-fractalkine antibody is administered to a human by single-dose intravenous administration at a dose of 10 mg/kg of human body weight, the mean $AUC_{(0-336h)}$ of the anti-fractalkine antibody is a value included in the numerical range of 80% to 125% of $3.8\times10^4$ μg·h/mL.

In a preferred embodiment of the present invention, the anti-FKN antibody is the antibody H3-2L4, which consists of a heavy chain consisting of the amino acid sequence shown in SEQ ID NO: 11

(QVQLVQSGAEVKKPGASVKVSCKASGYTFTNYYIHWVKQAPGQGLEWI

GWIYPGDGSPKFNERFKGRTTLTADKSTNTAYMLLSSLRSEDTAVYFCA

TGPTDGDYFDYWGQGTTVTVSSASTKGPSVFPLAPCSRSTSESTAALGC

LVKDYFPEPVTVSWNSGALTSGVHTFPAVLQSSGLYSLSSVVTVPSSNF

GTQTYTCNVDHKPSNTKVDKTVERKCCVECPPCPAPPAAAPSVFLFPPK

PKDTLMISRTPEVTCVVVDVSHEDPEVQFNWYVDGVEVHNAKTKPREEQ

FNSTFRVVSVLTVVHQDWLNGKEYKCKVSNKGLPAPIEKTISKTKGQPR

EPQVYTLPPSREEMTKNQVSLTCLVKGFYPSDIAVEWESNGQPENNYKT

TPPMLDSDGSFFLYSKLTVDKSRWQQGNVFSCSVMHEALHNHYTQKSLS

LSPGK)

and a light chain consisting of the amino acid sequence shown in SEQ ID NO: 12

(DIQMTQSPSSLSASVGDRVTITCRASGNIHNFLAWYQQKPGKAPKLLI

YNEKTLADGVPSRFSGSGSGTDYTLTISSLQPEDFATYFCQQFWSTPYT

FGGGTKVEIKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC).

4. Dose, Dosing Intervals, and Number of Doses

The pharmaceutical composition or anti-FKN antibody of the present invention is administered to a human subject at a dose that provides to the subject, the serum concentration of an anti-FKN antibody that is therapeutically effective for Crohn's disease. For example, the pharmaceutical composition or anti-FKN antibody of the present invention is administered, such that the blood concentration or mean trough concentration of the anti-FKN antibody is 20 μg/mL or more, 30 μg/mL or more, 40 μg/mL or more, 50 μg/mL or more, 60 μg/mL or more, 70 μg/mL or more, or 80 μg/mL or more. Preferably, the pharmaceutical composition or anti-FKN antibody of the present invention is administered by multiple-dose administration, such that the mean trough concentration of the anti-FKN antibody is 70 μg/mL or more, or 80 μg/mL or more.

In one embodiment of the present invention, the pharmaceutical composition or anti-FKN antibody of the present invention is used, such that the anti-FKN antibody is intravenously administered to a human at a dose of at least 10 mg/kg of human body weight. In another embodiment of the present invention, the pharmaceutical composition or anti-FKN antibody of the present invention is used, such that the anti-FKN antibody is intravenously administered to a human at a dose of 10 mg/kg of human body weight to 15 mg/kg of human body weight. In one embodiment of the present invention, the pharmaceutical composition or anti-FKN antibody of the present invention is used, such that the anti-FKN antibody is intravenously administered to a human at a dose of 10 mg/kg of human body weight or 15 mg/kg of human body weight.

The number of doses and the dosing intervals of the pharmaceutical composition or anti-FKN antibody of the present invention can be changed depending on the amount of the anti-FKN antibody in a single administration and the administration route.

In one embodiment of the present invention, the pharmaceutical composition or anti-FKN antibody of the present invention is used, such that the anti-FKN antibody is administered to a human subject in need thereof by multiple-dose intravenous administration, at a single dose of at least 10 mg/kg of human body weight, at dosing intervals from once every week to once two months. In another embodiment of the present invention, the pharmaceutical composition or anti-FKN antibody of the present invention is used, such that the anti-FKN antibody is administered to a human subject in need thereof by multiple-dose intravenous administration, at a single dose of at least 10 mg/kg of human body weight, at dosing intervals from once every week to once one month. In another embodiment of the present invention, the pharmaceutical composition or anti-FKN antibody of the present invention is used, such that the anti-FKN antibody is administered to a human subject in need thereof by multiple-dose intravenous administration, at a single dose of at least 10 mg/kg of human body weight, at dosing intervals from once every week to once every two weeks. In a specific embodiment of the present invention, the pharmaceutical composition or anti-FKN antibody of the present invention is used, such that the anti-FKN antibody is intravenously administered, at a single dose of at least 10 mg/kg of human body weight, at dosing intervals of once every week two times, and then at dosing intervals of every other week.

In another embodiment of the present invention, the pharmaceutical composition or anti-FKN antibody of the present invention is used, such that the anti-FKN antibody is administered to a human subject in need thereof by multiple-dose intravenous administration, at a single dose of 10 to 15 mg/kg of human body weight, at dosing intervals from once every week to once two months. In another embodiment of the present invention, the pharmaceutical composition or anti-FKN antibody of the present invention is used, such that the anti-FKN antibody is administered to a human subject in need thereof by multiple-dose intravenous administration, at a single dose of 10 to 15 mg/kg of human body weight, at dosing intervals from once every week to once one month. In another embodiment of the present invention, the pharmaceutical composition or anti-FKN antibody of the present invention is used, such that the anti-FKN antibody is administered to a human subject in need thereof by multiple-dose intravenous administration, at a single dose of 10 to 15 mg/kg of human body weight, at dosing intervals from once every week to once every two weeks. In a specific embodiment of the present invention, the pharmaceutical composition or anti-FKN antibody of the present invention is used, such that the anti-FKN antibody is intravenously administered to a human subject in need thereof, at a single dose of 10 to 15 mg/kg of human body weight, at dosing intervals of once every week two times, and then at dosing intervals of every other week.

In another embodiment of the present invention, the pharmaceutical composition or anti-FKN antibody of the present invention is used, such that the anti-FKN antibody is administered to a human subject in need thereof by multiple-dose intravenous administration, at a single dose of 10 mg/kg of human body weight or 15 mg/kg of human body weight, at dosing intervals from once every week to once two months. In another embodiment of the present invention, the pharmaceutical composition or anti-FKN antibody of the present invention is used, such that the anti-FKN antibody is administered to a human subject in need thereof by multiple-dose intravenous administration, at a single dose of 10 mg/kg of human body weight or 15 mg/kg of human body weight, at dosing intervals from once every week to once one month. In another embodiment of the present invention, the pharmaceutical composition or anti-FKN antibody of the present invention is used, such that the anti-FKN antibody is administered to a human subject in need thereof by multiple-dose intravenous administration, at a single dose of 10 mg/kg of human body weight or 15 mg/kg of human body weight, at dosing intervals from once every week to once every two weeks. In a specific embodiment of the present invention, the pharmaceutical composition or anti-FKN antibody of the present invention is used, such that the anti-FKN antibody is intravenously administered to a human subject in need thereof, at a dose of 10 mg/kg of human body weight or 15 mg/kg of human body weight, at dosing intervals of once every week two times, and then at dosing intervals of every other week.

The number of doses of the pharmaceutical composition or anti-FKN antibody of the present invention is not particularly limited, as long as it provides therapeutically effective improvement to Crohn's disease, and it can be changed depending on the amount of the anti-FKN antibody administered as a single dose, the administration route, and dosing intervals.

In one embodiment of the present invention, the pharmaceutical composition or anti-FKN antibody of the present invention can be intravenously administered to a subject at dosing intervals from once every week to once two months, at least 2 times, at least 3 times, at least 4 times, at least 5 times, at least 6 times, at least 7 times, at least 8 times, at least 9 times, at least 10 times, at least 11 times, at least 12 times, at least 13 times, at least 14 times, at least 15 times, at least 16 times, at least 17 times, at least 18 times, at least 19 times, at least 20 times, at least 21 times, at least 22 times, at least 23 times, at least 24 times, at least 25 times, at least 26 times, at least 27 times, or more times.

In another embodiment of the present invention, the pharmaceutical composition or anti-FKN antibody of the present invention can be intravenously administered to a subject at dosing intervals from once every week to once one month, at least 2 times, at least 3 times, at least 4 times, at least 5 times, at least 6 times, at least 7 times, at least 8 times, at least 9 times, at least 10 times, at least 11 times, at least 12 times, at least 13 times, at least 14 times, at least 15 times, at least 16 times, at least 17 times, at least 18 times, at least 19 times, at least 20 times, at least 21 times, at least 22 times, at least 23 times, at least 24 times, at least 25 times, at least 26 times, at least 27 times, or more times.

In a further embodiment of the present invention, the pharmaceutical composition or anti-FKN antibody of the present invention can be intravenously administered to a subject at dosing intervals from once every week to once every two weeks, at least 2 times, at least 3 times, at least 4 times, at least 5 times, at least 6 times, at least 7 times, at least 8 times, at least 9 times, at least 10 times, at least 11 times, at least 12 times, at least 13 times, at least 14 times, at least 15 times, at least 16 times, at least 17 times, at least 18 times, at least 19 times, at least 20 times, at least 21 times, at least 22 times, at least 23 times, at least 24 times, at least 25 times, at least 26 times, at least 27 times, or more times.

In a specific embodiment of the present invention, the pharmaceutical composition or anti-FKN antibody of the present invention can be intravenously administered to a subject at dosing intervals of once every week two times, and then at dosing intervals of every other week, at least 2 times, at least 3 times, at least 4 times, at least 5 times, at least 6 times, at least 7 times, at least 8 times, at least 9 times, at least 10 times, at least 11 times, at least 12 times, at least 13 times, at least 14 times, at least 15 times, at least 16 times, at least 17 times, at least 18 times, at least 19 times, at least 20 times, at least 21 times, at least 22 times, at least 23 times, at least 24 times, at least 25 times, at least 26 times, at least 27 times, or more times.

In a specific embodiment of the present invention, the pharmaceutical composition or anti-FKN antibody of the present invention can be intravenously administered to a subject at dosing intervals from once every week to once two months, at least 2 times, at least 3 times, at least 4 times, at least 5 times, at least 6 times, at least 7 times, at least 8 times, at least 9 times, at least 10 times, at least 11 times, at least 12 times, at least 13 times, at least 14 times, at least 15 times, at least 16 times, at least 17 times, at least 18 times, at least 19 times, at least 20 times, at least 21 times, at least 22 times, at least 23 times, at least 24 times, at least 25 times, at least 26 times, at least 27 times, or more times, such that the mean trough concentration of the anti-FKN antibody is 20 μg/mL or more, 30 μg/mL or more, 40 μg/mL or more, 50 μg/mL or more, 60 μg/mL or more, 70 μg/mL or more, or 80 μg/mL or more.

In a further embodiment of the present invention, the pharmaceutical composition or anti-FKN antibody of the present invention can be intravenously administered to a subject at dosing intervals from once every week to once one month, at least 2 times, at least 3 times, at least 4 times, at least 5 times, at least 6 times, at least 7 times, at least 8 times, at least 9 times, at least 10 times, at least 11 times, at least 12 times, at least 13 times, at least 14 times, at least 15 times, at least 16 times, at least 17 times, at least 18 times, at least 19 times, at least 20 times, at least 21 times, at least 22 times, at least 23 times, at least 24 times, at least 25 times, at least 26 times, at least 27 times, or more times, such that the mean trough concentration of the anti-FKN antibody is 20 μg/mL or more, 30 μg/mL or more, 40 μg/mL or more, 50 μg/mL or more, 60 μg/mL or more, 70 μg/mL or more, or 80 μg/mL or more.

In a further embodiment of the present invention, the pharmaceutical composition or anti-FKN antibody of the present invention can be intravenously administered to a subject at dosing intervals from once every week to once every two weeks, at least 2 times, at least 3 times, at least 4 times, at least 5 times, at least 6 times, at least 7 times, at least 8 times, at least 9 times, at least 10 times, at least 11 times, at least 12 times, at least 13 times, at least 14 times, at least 15 times, at least 16 times, at least 17 times, at least 18 times, at least 19 times, at least 20 times, at least 21 times, at least 22 times, at least 23 times, at least 24 times, at least 25 times, at least 26 times, at least 27 times, or more times, such that the mean trough concentration of the anti-FKN antibody is 20 μg/mL or more, 30 μg/mL or more, 40 μg/mL or more, 50 μg/mL or more, 60 μg/mL or more, 70 μg/mL or more, or 80 μg/mL or more.

In a further embodiment of the present invention, the pharmaceutical composition or anti-FKN antibody of the present invention can be intravenously administered to a subject at dosing intervals of once every week two times, and then at dosing intervals of every other week, at least 2 times, at least 3 times, at least 4 times, at least 5 times, at least 6 times, at least 7 times, at least 8 times, at least 9 times, at least 10 times, at least 11 times, at least 12 times, at least 13 times, at least 14 times, at least 15 times, at least 16 times, at least 17 times, at least 18 times, at least 19 times, at least 20 times, at least 21 times, at least 22 times, at least 23 times, at least 24 times, at least 25 times, at least 26 times, at least 27 times, or more times, such that the mean trough concentration of the anti-FKN antibody is 20 μg/mL or more, 30 μg/mL or more, 40 μg/mL or more, 50 μg/mL or more, 60 μg/mL or more, 70 μg/mL or more, or 80 μg/mL or more.

Hereafter, specific aspects of the present invention will be described, but the aspects of the present invention are not limited thereto.

In one aspect, the present invention is a pharmaceutical composition for treating Crohn's disease, which comprises an anti-fractalkine antibody and a pharmaceutically acceptable excipient, wherein
the anti-fractalkine antibody is an antibody comprising:
a heavy chain variable region comprising the amino acid sequence shown in SEQ ID NO: 13

(QVQLVQSGAEVKKPGASVKVSCKASGYTFTNYYIHWVKQAPGQGLEWI

GWIYPGDGSPKFNERFKGRTTLTADKSTNTAYMLLSSLRSEDTAVYFCA

TGPTDGDYFDYWGQGTTVTVSS);

a light chain variable region comprising the amino acid sequence shown in SEQ ID NO: 14

(DIQMTQSPSSLSASVGDRVTITCRASGNIHNFLAWYQQKPGKAPKLLI

YNEKTLADGVPSRFSGSGSGTDYILTISSLQPEDFATYFCQQFWSTPYT

FGGGTKVEIK);

and
a constant region of human IgG2 isotype, wherein
the Fc region of the constant region of human IgG2 isotype comprises mutations V234A and G237A, and
the pharmaceutical composition is used, such that the anti-fractalkine antibody is intravenously administered to a human at a dose of at least 10 mg/kg of human body weight.

In another aspect, the present invention is a pharmaceutical composition for treating Crohn's disease, which comprises an anti-fractalkine antibody and a pharmaceutically acceptable excipient, wherein
the anti-fractalkine antibody is an antibody comprising:
a heavy chain variable region comprising the amino acid sequence shown in SEQ ID NO: 13

(QVQLVQSGAEVKKPGASVKVSCKASGYTFTNYYIHWVKQAPGQGLEWI

GWIYPGDGSPKFNERFKGRTTLTADKSTNTAYMLLSSLRSEDTAVYFCA

TGPTDGDYFDYWGQGTTVTVSS);

a light chain variable region comprising the amino acid sequence shown in SEQ ID NO: 14

(DIQMTQSPSSLSASVGDRVTITCRASGNIHNFLAWYQQKPGKAPKLLI

YNEKTLADGVPSRFSGSGSGTDYILTISSLQPEDFATYFCQQFWSTPYT

FGGGTKVEIK);

and
a constant region of human IgG2 isotype, wherein
the Fc region of the constant region of human IgG2 isotype comprises mutations V234A and G237A, and
the pharmaceutical composition is used, such that the anti-fractalkine antibody is intravenously administered to a human at a dose of 10 to 15 mg/kg of human body weight.

In a further aspect, the present invention is a pharmaceutical composition for treating Crohn's disease, which comprises an anti-fractalkine antibody and a pharmaceutically acceptable excipient, wherein
the anti-fractalkine antibody is an antibody comprising:
a heavy chain variable region comprising the amino acid sequence shown in SEQ ID NO: 13

(QVQLVQSGAEVKKPGASVKVSCKASGYTFTNYYIHWVKQAPGQGLEWI

GWIYPGDGSPKFNERFKGRTTLTADKSTNTAYMLLSSLRSEDTAVYFCA

TGPTDGDYFDYWGQGTTVTVSS);

a light chain variable region comprising the amino acid sequence shown in SEQ ID NO: 14

(DIQMTQSPSSLSASVGDRVTITCRASGNIHNFLAWYQQKPGKAPKLLI
YNEKTLADGVPSRFSGSGSGTDYILTISSLQPEDFATYFCQQFWSTPYT
FGGGTKVEIK);

and
a constant region of human IgG2 isotype, wherein
the Fc region of the constant region of human IgG2 isotype comprises mutations V234A and G237A, and
the pharmaceutical composition is used, such that the anti-fractalkine antibody is intravenously administered to a human at a dose of 10 mg/kg of human body weight or 15 mg/kg of human body weight.

In another aspect, the pharmaceutical composition of the present invention is administered to a human by repeated intravenous administration at dosing intervals from once every week to once every two weeks, such that it provides a mean trough concentration of the anti-FKN antibody that is 40 μg/mL or more. In a preferred embodiment, the pharmaceutical composition of the present invention is administered to a human by repeated intravenous administration at dosing intervals from once every week to once every two weeks, such that it provides a mean trough concentration of the anti-FKN antibody that is 60 μg/mL or more. In a more preferred embodiment, the pharmaceutical composition of the present invention is administered to a human by repeated intravenous administration at dosing intervals from once every week to once every two weeks, such that it provides a mean trough concentration of the anti-FKN antibody that is 80 μg/mL or more.

In a preferred embodiment, the pharmaceutical composition is a pharmaceutical composition, wherein when the pharmaceutical composition is administered to a human by single-dose intravenous administration, the mean $C_{max}$ of the anti-fractalkine antibody at a dose of 1 mg/kg of human body weight is 21 to 25 μg/mL.

In a preferred embodiment, the pharmaceutical composition is a pharmaceutical composition for intravenous administration, which is formulated, such that when the anti-fractalkine antibody is administered to a human by single-dose intravenous administration at a dose of 10 mg/kg of human body weight, it provides any one, or two, or three of the following pharmacokinetic parameters:
the mean $C_{max}$ of the anti-fractalkine antibody is a value included in the numerical range of 80% to 125% of $2.4 \times 10^2$ μg/mL;
the mean $AUC_{(0-t)}$ of the anti-fractalkine antibody is a value included in the numerical range of 80% to 125% of $7.0 \times 10^4$ μg·h/mL; and
the mean $AUC_{(0-336h)}$ of the anti-fractalkine antibody is a value included in the numerical range of 80% to 125% of $3.8 \times 10^4$ μg·h/mL.

In a preferred embodiment of the present invention, the anti-FKN antibody is the antibody H3-2L4, which consists of a heavy chain consisting of the amino acid sequence shown in SEQ ID NO: 11

(QVQLVQSGAEVKKPGASVKVSCKASGYTFTNYYIHWVKQAPGQGLEWI
GWIYPGDGSPKFNERFKGRTTLTADKSTNTAYMLLSSLRSEDTAVYFCA
TGPTDGDYFDYWGQGTTVTVSSASTKGPSVFPLAPCSRSTSESTAALGC
LVKDYFPEPVTVSWNSGALTSGVHTFPAVLQSSGLYSLSSVVTVPSSNF
GTQTYTCNVDHKPSNTKVDKTVERKCCVECPPCPAPPAAAPSVFLFPPK
PKDTLMISRTPEVTCVVVDVSHEDPEVQFNWYVDGVEVHNAKTKPREEQ
FNSTFRVVSVLTVVHQDWLNGKEYKCKVSNKGLPAPIEKTISKTKGQPR
EPQVYTLPPSREEMTKNQVSLTCLVKGFYPSDIAVEWESNGQPENNYKT
TPPMLDSDGSFFLYSKLTVDKSRWQQGNVFSCSVMHEALHNHYTQKSLS
LSPGK)

and a light chain consisting of the amino acid sequence shown in SEQ ID NO: 12

(DIQMTQSPSSLSASVGDRVTITCRASGNIHNFLAWYQQKPGKAPKLLI
YNEKTLADGVPSRFSGSGSGTDYTLTISSLQPEDFATYFCQQFWSTPYT
FGGGTKVEIKRTVAAPSVFIFPPSDEQLKSGTASVVCLLNNFYPREAKV
QWKVDNALQSGNSQESVTEQDSKDSTYSLSSTLTLSKADYEKHKVYACE
VTHQGLSSPVTKSFNRGEC).

In a preferred embodiment, the pharmaceutical composition is a pharmaceutical composition, which is administered to a human by multiple-dose intravenous administration at dosing intervals from once every week to once every two weeks.

In a preferred embodiment, the pharmaceutical composition is a pharmaceutical composition, which is intravenously administered, such that the mean trough concentration of the anti-fractalkine antibody is 80 μg/mL or more.

In a preferred embodiment, the pharmaceutical composition is a pharmaceutical composition, wherein the anti-fractalkine antibody is intravenously administered to a human at a dose of 10 mg/kg of human body weight or 15 mg/kg of human body weight at dosing intervals of once every week three times, and then at dosing intervals of every other week at least 7 times.

In one embodiment of the present invention, the pharmaceutical composition of the present invention is a pharmaceutical composition, in which when the anti-fractalkine antibody is administered to a human by multiple-dose intravenous administration at a single dose of at least 10 mg/kg of human body weight at dosing intervals from once every week to once every two weeks, the mean serum concentration of total FKN can be 200 ng/mL or more, 300 ng/mL or more, or 400 ng/mL or more.

In another embodiment of the present invention, the pharmaceutical composition of the present invention is a pharmaceutical composition, wherein when the anti-fractalkine antibody is administered to a human by multiple-dose intravenous administration at a single dose of 10 to 15 mg/kg of human body weight at dosing intervals from once every week to once every two weeks, the mean serum concentration of total FKN is 200 ng/mL or more, 300 ng/mL or more, or 400 ng/mL or more.

In another embodiment of the present invention, the pharmaceutical composition of the present invention is a pharmaceutical composition, wherein when the anti-fractalkine antibody is administered to a human by multiple-dose intravenous administration at a single dose of 10 mg/kg of human body weight or 15 mg/kg of human body weight at dosing intervals from once every week to once every two weeks, the mean serum concentration of total FKN is 200 ng/mL or more, 300 ng/mL or more, or 400 ng/mL or more.

In one embodiment of the present invention, the pharmaceutical composition of the present invention is a pharmaceutical composition, wherein when the anti-fractalkine antibody is administered to a human by multiple-dose intravenous administration at a single dose of at least 10 mg/kg of human body weight at dosing intervals from once every week to once every two weeks, the CDAI score at 12 weeks or more after initiation of the administration is reduced by 70 or more, and more preferably by 100 or more, with respect to the CDAI score before initiation of the administration.

In another embodiment of the present invention, the pharmaceutical composition of the present invention is a pharmaceutical composition, wherein when the anti-fractalkine antibody is administered to a human by multiple-dose intravenous administration at a single dose of 10 to 15 mg/kg of human body weight at dosing intervals from once every week to once every two weeks, the CDAI score at 12 weeks or more after initiation of the administration is reduced by 70 or more, and more preferably by 100 or more, with respect to the CDAI score before initiation of the administration.

In another embodiment of the present invention, the pharmaceutical composition of the present invention is a pharmaceutical composition, wherein when the anti-fractalkine antibody is administered to a human by multiple-dose intravenous administration at a single dose of 10 mg/kg of human body weight or 15 mg/kg of human body weight at dosing intervals from once every week to once every two weeks, the CDAI score at 12 weeks or more after initiation of the administration is reduced by 70 or more, and more preferably by 100 or more, with respect to the CDAI score before initiation of the administration.

In a preferred embodiment, the pharmaceutical composition of the present invention is a pharmaceutical composition, wherein the CDAI score at 12 weeks or more after initiation of the administration is reduced by 70 or more, and more preferably by 100 or more, with respect to the CDAI score before initiation of the administration, when the anti-fractalkine antibody is administered to a human having a CDAI score of 220 or greater before initiation of the administration by multiple-dose intravenous administration at a single dose of at least 10 mg/kg of human body weight at dosing intervals from once every week to once every two weeks.

In another preferred embodiment, the pharmaceutical composition of the present invention is a pharmaceutical composition, wherein the CDAI score at 12 weeks or more after initiation of the administration is reduced by 70 or more, and more preferably by 100 or more, with respect to the CDAI score before initiation of the administration, when the anti-fractalkine antibody is administered to a human having a CDAI score of 220 or greater before initiation of the administration by multiple-dose intravenous administration at a single dose of 10 to 15 mg/kg of human body weight at dosing intervals from once every week to once every two weeks.

In a further preferred embodiment, the pharmaceutical composition of the present invention is a pharmaceutical composition, wherein the CDAI score at 12 weeks or more after initiation of the administration is reduced by 70 or more, and more preferably by 100 or more, with respect to the CDAI score before initiation of the administration, when the anti-fractalkine antibody is administered to a human having a CDAI score of 220 or greater before initiation of the administration by multiple-dose intravenous administration at a single dose of 10 mg/kg of human body weight or 15 mg/kg of human body weight at dosing intervals from once every week to once every two weeks.

In a preferred embodiment, the pharmaceutical composition of the present invention is a pharmaceutical composition, wherein the CDAI score at 12 weeks or more after initiation of the administration is less than 150, when the anti-fractalkine antibody is administered to a human having a CDAI score of 220 or greater before initiation of the administration by multiple-dose intravenous administration at a single dose of at least 10 mg/kg of human body weight at dosing intervals from once every week to once every two weeks.

In another preferred embodiment, the pharmaceutical composition of the present invention is a pharmaceutical composition, wherein the CDAI score at 12 weeks or more after initiation of the administration is less than 150, when the anti-fractalkine antibody is administered to a human having a CDAI score of 220 or greater before initiation of the administration by multiple-dose intravenous administration at a single dose of 10 to 15 mg/kg of human body weight at dosing intervals from once every week to once every two weeks.

In a further preferred embodiment, the pharmaceutical composition of the present invention is a pharmaceutical composition, wherein the CDAI score at 12 weeks or more after initiation of the administration is less than 150, when the anti-fractalkine antibody is administered to a human having a CDAI score of 220 or greater before initiation of the administration by multiple-dose intravenous administration at a single dose of 10 mg/kg of human body weight or 15 mg/kg of human body weight at dosing intervals from once every week to once every two weeks.

In another aspect, the present invention relates to a method for treating Crohn's disease, comprising intravenously administering to a human in need thereof, an anti-fractalkine antibody at a dose of at least 10 mg/kg of human body weight, wherein
the anti-fractalkine antibody is an antibody comprising:
a heavy chain variable region comprising the amino acid sequence shown in SEQ ID NO: 13

(QVQLVQSGAEVKKPGASVKVSCKASGYTFTNYYIHWVKQAPGQGLEWI

GWIYPGDGSPKFNERFKGRTTLTADKSTNTAYMLLSSLRSEDTAVYFCA

TGPTDGDYFDYWGQGTTVTVSS);

a light chain variable region comprising the amino acid sequence shown in SEQ ID NO: 14

(DIQMTQSPSSLSASVGDRVTITCRASGNIHNFLAWYQQKPGKAPKLLI

YNEKTLADGVPSRFSGSGSGTDYILTISSLQPEDFATYFCQQFWSTPYT

FGGGTKVEIK);

and
a constant region of human IgG2 isotype, wherein
the Fc region of the constant region of human IgG2 isotype comprises mutations V234A and G237A.

In one embodiment, the present invention relates to a method for treating Crohn's disease, comprising intravenously administering to a human in need thereof, an anti-fractalkine antibody at a dose of 10 to 15 mg/kg of human body weight, wherein the anti-fractalkine antibody is an antibody comprising:
a heavy chain variable region comprising the amino acid sequence shown in SEQ ID NO: 13

(QVQLVQSGAEVKKPGASVKVSCKASGYTFTNYYIHWVKQAPGQGLEWI
GWIYPGDGSPKFNERFKGRTTLTADKSTNTAYMLLSSLRSEDTAVYFCA
TGPTDGDYFDYWGQGTTVTVSS);

a light chain variable region comprising the amino acid sequence shown in SEQ ID NO: 14

(DIQMTQSPSSLSASVGDRVTITCRASGNIHNFLAWYQQKPGKAPKLLIY
NEKTLADGVPSRFSGSGSGTDYILTISSLQPEDFATYFCQQFWSTPYTFG
GGTKVEIK);

and
a constant region of human IgG2 isotype, wherein
the Fc region of the constant region of human IgG2 isotype comprises mutations V234A and G237A.

In one embodiment, the present invention relates to a method for treating Crohn's disease, comprising administering to a human, an anti-fractalkine antibody at a dose of 10 mg/kg of human body weight or 15 mg/kg of human body weight, wherein
the anti-fractalkine antibody is an antibody comprising:
a heavy chain variable region comprising the amino acid sequence shown in SEQ ID NO: 13

(QVQLVQSGAEVKKPGASVKVSCKASGYTFTNYYIHWVKQAPGQGLEW
IGWIYPGDGSPKFNERFKGRTTLTADKSTNTAYMLLSSLRSEDTAVYF
CATGPTDGDYFDYWGQGTTVTVSS);

a light chain variable region comprising the amino acid sequence shown in SEQ ID NO: 14

(DIQMTQSPSSLSASVGDRVTITCRASGNIHNFLAWYQQKPGKAPKL
LIYNEKTLADGVPSRFSGSGSGTDYILTISSLQPEDFATYFCQQFWS
TPYTFGGGTKVEIK);

and
a constant region of human IgG2 isotype, wherein
the Fc region of the constant region of human IgG2 isotype comprises mutations V234A and G237A.

In another aspect, the present invention relates to a pharmaceutical composition for use in a method for Crohn's disease, wherein
the pharmaceutical composition comprises an anti-fractalkine antibody and a pharmaceutically acceptable excipient, and
the therapeutic method comprises administering a therapeutically effective amount of the anti-fractalkine antibody to a human in need thereof by intravenous administration of the pharmaceutical composition, which is formulated, such that it provides a mean $C_{max}$ of the anti-fractalkine antibody at a dose of 1 mg/kg of human body weight that is 21 to 25 µg/mL, wherein
the anti-fractalkine antibody is an antibody comprising:
a heavy chain variable region comprising the amino acid sequence shown in SEQ ID NO: 13

(QVQLVQSGAEVKKPGASVKVSCKASGYTFTNYYIHWVKQAPGQGLEWI
GWIYPGDGSPKFNERFKGRTTLTADKSTNTAYMLLSSLRSEDTAVYFCA
TGPTDGDYFDYWGQGTTVTVSS);

a light chain variable region comprising the amino acid sequence shown in SEQ ID NO: 14

(DIQMTQSPSSLSASVGDRVTITCRASGNIHNFLAWYQQKPGKAPKLL
IYNEKTLADGVPSRFSGSGSGTDYILTISSLQPEDFATYFCQQFWSTP
YTFGGGTKVEIK);

and
a constant region of human IgG2 isotype, wherein
the Fc region of the constant region of human IgG2 isotype comprises mutations V234A and G237A.

In another aspect, the present invention relates to a pharmaceutical composition for use in a method for treating Crohn's disease, wherein
the pharmaceutical composition comprises an anti-fractalkine antibody and a pharmaceutically acceptable excipient, and
the therapeutic method comprises administering a therapeutically effective amount of the anti-fractalkine antibody to a human in need thereof by intravenous administration of the pharmaceutical composition, which is formulated, such that it provides any one, or two, or three of the following pharmacokinetic parameters:
when the anti-fractalkine antibody is administered to a human by single-dose intravenous administration at a dose of 10 mg/kg of human body weight, the mean $C_{max}$ of the anti-fractalkine antibody is a value included in the numerical range of 80% to 125% of $2.4 \times 10^2$ µg/mL;
when the anti-fractalkine antibody is administered to a human by single-dose intravenous administration at a dose of 10 mg/kg of human body weight, the mean $AUC_{(0-t)}$ of the anti-fractalkine antibody is a value included in the numerical range of 80% to 125% of $7.0 \times 10^4$ µg·h/mL; and
when the anti-fractalkine antibody is administered to a human by single-dose intravenous administration at a dose of 10 mg/kg of human body weight, the mean $AUC_{(0-336h)}$ of the anti-fractalkine antibody is a value included in the numerical range of 80% to 125% of $3.8 \times 10^4$ µg·h/mL, wherein
the anti-fractalkine antibody is an antibody comprising:
a heavy chain variable region comprising the amino acid sequence shown in SEQ ID NO: 13

(QVQLVQSGAEVKKPGASVKVSCKASGYTFTNYYIHWVKQAPGQGLEW
IGWIYPGDGSPKFNERFKGRTTLTADKSTNTAYMLLSSLRSEDTAVYF
CATGPTDGDYFDYWGQGTTVTVSS);

a light chain variable region comprising the amino acid sequence shown in SEQ ID NO: 14

(DIQMTQSPSSLSASVGDRVTITCRASGNIHNFLAWYQQKPGKAPKLL
IYNEKTLADGVPSRFSGSGSGTDYILTISSLQPEDFATYFCQQFWSTP
YTFGGGTKVEIK);

and
a constant region of human IgG2 isotype, wherein
the Fc region of the constant region of human IgG2 isotype comprises mutations V234A and G237A.

In another aspect, the present invention relates to a pharmaceutical composition for use in a method for treating Crohn's disease, wherein the pharmaceutical composition comprises an anti-fractalkine antibody and a pharmaceutically acceptable excipient, and the therapeutic method comprises intravenously administering a therapeutically effective amount of the anti-fractalkine antibody to a human in need thereof, wherein the anti-fractalkine antibody is an antibody comprising:
a heavy chain variable region comprising the amino acid sequence shown in SEQ ID NO: 13

(QVQLVQSGAEVKKPGASVKVSCKASGYTFTNYYIHWVKQAPGQGLEW

IGWIYPGDGSPKFNERFKGRTTLTADKSTNTAYMLLSSLRSEDTAVYF

CATGPTDGDYFDYWGQGTTVTVSS);

a light chain variable region comprising the amino acid sequence shown in SEQ ID NO: 14

(DIQMTQSPSSLSASVGDRVTITCRASGNIHNFLAWYQQKPGKAPKLL

IYNEKTLADGVPSRFSGSGSGTDYILTISSLQPEDFATYFCQQFWSTP

YTFGGGTKVEIK);

and
a constant region of human IgG2 isotype, wherein
the Fc region of the constant region of human IgG2 isotype comprises mutations V234A and G237A, wherein the therapeutically effective amount is a dose, which provides any one, or two, or three of the following pharmacokinetic parameters when the therapeutically effective amount of the anti-fractalkine antibody is administered by single-dose intravenous administration of the pharmaceutical composition comprising the anti-fractalkine antibody:

the mean $C_{max}$ of the anti-fractalkine antibody is a value included in the numerical range of 80% to 125% of $2.4\times10^2$ µg/mL;

the mean $AUC_{(0-t)}$ of the anti-fractalkine antibody is a value included in the numerical range of 80% to 125% of $7.0\times10^4$ µg·h/mL; and the mean $AUC_{(0-336h)}$ of the anti-fractalkine antibody is a value included in the numerical range of 80% to 125% of $3.8\times10^4$ µg·h/mL.

In another aspect, the present invention relates to a method for treating Crohn's disease, comprising administering a therapeutically effective amount of an anti-fractalkine antibody to a human in need thereof by intravenous administration of a pharmaceutical composition, which is formulated, such that it provides a mean $C_{max}$ of the anti-fractalkine antibody at a dose of 1 mg/kg of human body weight that is 21 to 25 µg/mL, wherein the anti-fractalkine antibody is an antibody comprising:
a heavy chain variable region comprising the amino acid sequence shown in SEQ ID NO: 13

(QVQLVQSGAEVKKPGASVKVSCKASGYTFTNYYIHWVKQAPGQGLEW

IGWIYPGDGSPKFNERFKGRTTLTADKSTNTAYMLLSSLRSEDTAVYF

CATGPTDGDYFDYWGQGTTVTVSS);

a light chain variable region comprising the amino acid sequence shown in SEQ ID NO: 14

(DIQMTQSPSSLSASVGDRVTITCRASGNIHNFLAWYQQKPGKAPKLLI

YNEKTLADGVPSRFSGSGSGTDYILTISSLQPEDFATYFCQQFWSTPYT

FGGGTKVEIK);

and
a constant region of human IgG2 isotype, wherein
the Fc region of the constant region of human IgG2 isotype comprises mutations V234A and G237A.

In another aspect, the present invention relates to a method for treating Crohn's disease, comprising administering a therapeutically effective amount of an anti-fractalkine antibody to a human in need thereof by intravenous administration of a pharmaceutical composition, which is formulated, such that it provides any one, or two, or three of the following pharmacokinetic parameters:

when the anti-fractalkine antibody is administered to a human by single-dose intravenous administration at a dose of 10 mg/kg of human body weight, the mean $C_{max}$ of the anti-fractalkine antibody is a value included in the numerical range of 80% to 125% of $2.4\times10^2$ µg/mL;

when the anti-fractalkine antibody is administered to a human by single-dose intravenous administration at a dose of 10 mg/kg of human body weight, the mean $AUC_{(0-t)}$ of the anti-fractalkine antibody is a value included in the numerical range of 80% to 125% of $7.0\times10^4$ µg·h/mL; and when the anti-fractalkine antibody is administered to a human by single-dose intravenous administration at a dose of 10 mg/kg of human body weight, the mean $AUC_{(0-336h)}$ of the anti-fractalkine antibody is a value included in the numerical range of 80% to 125% of $3.8\times10^4$ µg·h/mL, wherein the anti-fractalkine antibody is an antibody comprising:
a heavy chain variable region comprising the amino acid sequence shown in SEQ ID NO: 13

(QVQLVQSGAEVKKPGASVKVSCKASGYTFTNYYIHWVKQAPGQGLEW

IGWIYPGDGSPKFNERFKGRTTLTADKSTNTAYMLLSSLRSEDTAVYF

CATGPTDGDYFDYWGQGTTVTVSS);

a light chain variable region comprising the amino acid sequence shown in SEQ ID NO: 14

(DIQMTQSPSSLSASVGDRVTITCRASGNIHNFLAWYQQKPGKAPKLL

IYNEKTLADGVPSRFSGSGSGTDYILTISSLQPEDFATYFCQQFWSTP

YTFGGGTKVEIK);

and
a constant region of human IgG2 isotype, wherein
the Fc region of the constant region of human IgG2 isotype comprises mutations V234A and G237A.

In the therapeutic method of the present invention, the anti-fractalkine antibody is administered to a human by repeated intravenous administration at dosing intervals from once every week to once every two weeks, such that it provides a mean trough concentration of the anti-FKN antibody that is 40 µg/mL or more. In a preferred embodiment, in the therapeutic method of the present invention, the anti-fractalkine antibody is administered to a human by repeated intravenous administration at dosing intervals from once every week to once every two weeks, such that it provides a mean trough concentration of the anti-FKN antibody that is 60 µg/mL or more. In a more preferred embodiment, in the therapeutic method of the present invention, the anti-fractalkine antibody is administered to a human by repeated intravenous administration at dosing intervals from once every week to once every two weeks, such that it provides a mean trough concentration of the anti-FKN antibody that is 80 µg/mL or more.

In a preferred embodiment, in the therapeutic method, the therapeutically effective amount of the anti-FKN antibody is administered in the form of a pharmaceutical composition for intravenous administration, which is formulated, such that when the anti-fractalkine antibody is administered to a human by single-dose intravenous administration at a dose of 1 mg/kg of human body weight, it provides a mean $C_{max}$ of the anti-fractalkine antibody that is a value of 21 to 25 µg/mL.

In a preferred embodiment, in the therapeutic method, the therapeutically effective amount of the anti-FKN antibody is administered in the form of a pharmaceutical composition for intravenous administration, which is formulated, such that when the anti-fractalkine antibody is administered to a human by single-dose intravenous administration at a dose of 10 mg/kg of human body weight, it provides any one, or two, or three of the following pharmacokinetic parameters:

the mean $C_{max}$ of the anti-fractalkine antibody is a value included in the numerical range of 80% to 125% of $2.4 \times 10^2$ µg/mL;

the mean $AUC_{(0-t)}$ of the anti-fractalkine antibody is a value included in the numerical range of 80% to 125% of $7.0 \times 10^4$ µg·h/mL; and the mean $AUC_{(0-336h)}$ of the anti-fractalkine antibody is a value included in the numerical range of 80% to 125% of $3.8 \times 10^4$ µg·h/mL.

In a preferred embodiment, the anti-fractalkine antibody is the antibody H3-2L4, which consists of a heavy chain consisting of the amino acid sequence shown in SEQ ID NO: 11

(QVQLVQSGAEVKKPGASVKVSCKASGYTFTNYYIHWVKQAPGQGLEW

IGWIYPGDGSPKFNERFKGRTTLTADKSTNTAYMLLSSLRSEDTAVYF

CATGPTDGDYFDYWGQGTTVTVSSASTKGPSVFPLAPCSRSTSESTAA

LGCLVKDYFPEPVTVSWNSGALTSGVHTFPAVLQSSGLYSLSSVVTVP

SSNFGTQTYTCNVDHKPSNTKVDKTVERKCCVECPPCPAPPAAAPSVF

LFPPKPKDTLMISRTPEVTCVVVDVSHEDPEVQFNWYVDGVEVHNAKT

KPREEQFNSTFRVVSVLTVVHQDWLNGKEYKCKVSNKGLPAPIEKTIS

KTKGQPREPQVYTLPPSREEMTKNQVSLTCLVKGFYPSDIAVEWESNG

QPENNYKTTPPMLDSDGSFFLYSKLTVDKSRWQQGNVFSCSVMHEALH

NHYTQKSLSLSPGK)

and a light chain consisting of the amino acid sequence shown in SEQ ID NO: 12

(DIQMTQSPSSLSASVGDRVTITCRASGNIHNFLAWYQQKPGKAPKLL

IYNEKTLADGVPSRFSGSGSGTDYTLTISSLQPEDFATYFCQQFWSTP

YTFGGGTKVEIKRTVAAPSVFIFPPSDEQLKSGTASVVCLLNNFYPRE

AKVQWKVDNALQSGNSQESVTEQDSKDSTYSLSSTLTLSKADYEKHKV

YACEVTHQGLSSPVTKSFNRGEC).

In a preferred embodiment, in the therapeutic method of Crohn's disease, the anti-fractalkine antibody is administered to a human by multiple-dose intravenous administration at dosing intervals from once every week to once every two weeks.

In a preferred embodiment, in the therapeutic method of Crohn's disease, the anti-fractalkine antibody is intravenously administered, such that the mean trough concentration of the anti-fractalkine antibody is 80 µg/mL or more.

In a preferred embodiment, in the therapeutic method of Crohn's disease, the anti-fractalkine antibody is intravenously administered to a human, at a dose of 10 mg/kg of human body weight, at dosing intervals of once every week 3 times, and then at dosing intervals of every other week at least 7 times.

In one embodiment of the present invention, in the therapeutic method of Crohn's disease of the present invention, a formulation for intravenous administration, which is formulated, such that when the anti-fractalkine antibody is administered to a human by multiple-dose intravenous administration at a single dose of at least 10 mg/kg of human body weight at dosing intervals from once every week to once every two weeks, the mean serum concentration of total FKN is 200 ng/mL or more, 300 ng/mL or more, or 400 ng/mL or more, is used.

In another embodiment of the present invention, in the therapeutic method of Crohn's disease of the present invention, a formulation for intravenous administration, which is formulated, such that when the anti-fractalkine antibody is administered to a human by multiple-dose intravenous administration at a single dose of 10 to 15 mg/kg of human body weight at dosing intervals from once every week to once every two weeks, the mean serum concentration of total FKN is 200 ng/mL or more, 300 ng/mL or more, or 400 ng/mL or more, is used.

In another embodiment of the present invention, in the therapeutic method of Crohn's disease of the present invention, a formulation for intravenous administration, which is formulated, such that when the anti-fractalkine antibody is administered to a human by multiple-dose intravenous administration at a single dose of 10 mg/kg of human body weight or 15 mg/kg of human body weight at dosing intervals from once every week to once every two weeks, the mean serum concentration of total FKN is 200 ng/mL or more, 300 ng/mL or more, or 400 ng/mL or more, is used.

In one embodiment of the present invention, in the therapeutic method of Crohn's disease of the present invention, a formulation for intravenous administration, which is formulated, such that when the anti-fractalkine antibody is administered to a human by multiple-dose intravenous administration at a single dose of at least 10 mg/kg of human body weight at dosing intervals from once every week to once every two weeks, the CDAI score at 12 weeks or more after initiation of the administration is reduced by 70 or more, and more preferably by 100 or more, with respect to the CDAI score before initiation of the administration, is used.

In another embodiment of the present invention, in the therapeutic method of Crohn's disease of the present invention, a formulation for intravenous administration, which is formulated, such that when the anti-fractalkine antibody is administered to a human by multiple-dose intravenous administration at a single dose of 10 to 15 mg/kg of human body weight at dosing intervals from once every week to once every two weeks, the CDAI score at 12 weeks or more after initiation of the administration is reduced by 70 or more, and more preferably by 100 or more, with respect to the CDAI score before initiation of the administration, is used.

In another embodiment of the present invention, in the therapeutic method of Crohn's disease of the present invention, a formulation for intravenous administration, which is formulated, such that when the anti-fractalkine antibody is administered to a human by multiple-dose intravenous administration at a single dose of 10 mg/kg of human body weight or 15 mg/kg of human body weight at dosing intervals from once every week to once every two weeks, the CDAI score at 12 weeks or more after initiation of the administration is reduced by 70 or more, and more preferably by 100 or more, with respect to the CDAI score before initiation of the administration.

In a preferred embodiment, in the therapeutic method of Crohn's disease of the present invention, a formulation for intravenous administration, which is formulated, such that when the anti-fractalkine antibody is administered to a human having a CDAI score of 220 or greater before initiation of the administration by multiple-dose intravenous administration at a single dose of at least 10 mg/kg of human body weight at dosing intervals from once every week to once every two weeks, the CDAI score at 12 weeks or more after initiation of the administration is reduced by 70 or more, and more preferably by 100 or more, with respect to the CDAI score before initiation of the administration, is used.

In another preferred embodiment, in the therapeutic method of Crohn's disease of the present invention, a formulation for intravenous administration, which is formulated, such that when the anti-fractalkine antibody is administered to a human having a CDAI score of 220 or greater before initiation of the administration by multiple-dose intravenous administration at a single dose of 10 to 15 mg/kg of human body weight at dosing intervals from once every week to once every two weeks, the CDAI score at 12 weeks or more after initiation of the administration is reduced by 70 or more, and more preferably by 100 or more, with respect to the CDAI score before initiation of the administration, is used.

In a further preferred embodiment, in the therapeutic method of Crohn's disease of the present invention, a formulation for intravenous administration, which is formulated, such that when the anti-fractalkine antibody is administered to a human having a CDAI score of 220 or greater before initiation of the administration by multiple-dose intravenous administration at a single dose of 10 mg/kg of human body weight or 15 mg/kg of human body weight at dosing intervals from once every week to once every two weeks, the CDAI score at 12 weeks or more after initiation of the administration is reduced by 70 or more, and more preferably by 100 or more, with respect to the CDAI score before initiation of the administration, is used.

In a preferred embodiment, in the therapeutic method of Crohn's disease of the present invention, a formulation for intravenous administration, which is formulated, such that when the anti-fractalkine antibody is administered to a human having a CDAI score of 220 or greater before initiation of the administration by multiple-dose intravenous administration at a single dose of at least 10 mg/kg of human body weight at dosing intervals from once every week to once every two weeks, the CDAI score at 12 weeks or more after initiation of the administration is less than 150, is used.

In another preferred embodiment, in the therapeutic method of Crohn's disease of the present invention, a formulation for intravenous administration, which is formulated, such that when the anti-fractalkine antibody is administered to a human having a CDAI score of 220 or greater before initiation of the administration by multiple-dose intravenous administration at a single dose of 10 to 15 mg/kg of human body weight at dosing intervals from once every week to once every two weeks, the CDAI score at 12 weeks or more after initiation of the administration is less than 150, is used.

In a further preferred embodiment, in the therapeutic method of Crohn's disease of the present invention, a formulation for intravenous administration, which is formulated, such that when the anti-fractalkine antibody is administered to a human having a CDAI score of 220 or greater before initiation of the administration by multiple-dose intravenous administration at a single dose of 10 mg/kg of human body weight or 15 mg/kg of human body weight at dosing intervals from once every week to once every two weeks, the CDAI score at 12 weeks or more after initiation of the administration is less than 150, is used.

In one embodiment of the present invention, the "human" is a Crohn's disease patient who has not obtained sufficient effects from corticosteroid or an immunomodulator, or who has not had continuous effects therefrom, or who has been intolerant thereto, or has not obtained sufficient effects from anti-TNF antibody.

A person skilled in the art should understand that any one or more of all any given aspects described in the present description may be combined, as appropriate, to carry out the present invention, unless it includes technical contradiction. Moreover, such a skilled person should understand that it will be preferable to combine all of preferred or advantageous aspects described in the present description, as appropriate, to carry out the present invention, unless it includes technical contradiction.

It should be considered that the disclosures of all publications cited in the present description are apparently incorporated herein by reference in their entirety. A person skilled in the art can understand that the relevant disclosures of these publications are incorporated in the present description as a part thereof according to the context thereof, without deviating from the spirit and scope of the present invention.

The publications cited in the present description are provided only for the purpose of disclosing related art prior to the filing date of the present application, and it must not be interpreted that the present inventors acknowledge that they do not have lights preceding the disclosures, for prior invention or other any given reasons. All descriptions of these publications are based on information which are available to the present applicant, and it does not mean at all that the applicant acknowledges that all of these contents are accurate.

The terms used in the present description are used to describe specific embodiments, and they are not intended to limit the scope of the invention.

The terms "comprise" and "include" are used in the present description to intend that the described matter (a member, a step, an element, a number, etc.) is present, except in a case where it should be contextually apparently understood in a different way, and it does not exclude the presence of other matters (members, steps, elements, numbers, etc.). The term "consist of" includes the aspects indicated with the term "consist of" and/or "consist essentially of."

Unless otherwise specified, all of the terms used herein (including technical terms and scientific terms) have the same meanings as those that are broadly understood by a person skilled in the art to which the present invention pertains. Unless otherwise clearly specified, the terms used herein should be interpreted to have meanings that are consistent with the meanings in the present description and the related technical field, and the terms should not be interpreted to have ideal or excessively formal meanings.

The terms, such as a "first," a "second," and the like, are used to express various elements. It is understood that these elements should not be limited by these terms. These terms are only used to distinguish one element from another element, and thus, for example, it is possible to describe a first element as a second element, and likewise, to describe a second element as a first element, without deviating from the scope of the present invention.

In the present description, it should be understood that numerical values used to express the contents of components or numerical ranges and the like are modified with the term "approximately," unless otherwise clearly specified. For example, the term "10 μg" is understood to mean "approximately 10 μg," unless otherwise clearly specified. Accordingly, it is natural that a person killed in the art can theoretically understand the degree of a numerical value according to common technical knowledge and the context of the present description.

Except in a case where an aspect contextually apparently has another meaning, when an aspect that is given in a singular form is used in the present description and claims, it is understood that such an aspect may also have a plural form, and vice versa, unless it includes technical contradiction.

Hereinafter, the present invention will be described in more detail with reference to the following examples. However, the present invention can be realized by various aspects, and thus, it must not be interpreted that the present invention is limited to the examples described herein. The present invention can be carried out with various modifications, additions, deletions, substitutions and the like by those skilled in the related art, without changing the spirit or scope of the present invention.

The abbreviations used in the following examples are commonly used abbreviations that are well known to a person skilled in the art. Several abbreviations will be described below.

AUC: area under the serum concentration-time curve
$AUC_{(0-inf)}$: area under the serum concentration-time curve from zero time extrap-olated to infinite time
$AUC_{(0-t)}$: area under the concentration-time curve from zero time to time of last quantifiable concentration
$AUC_{(0-336h)}$: area under the concentration-time curve from zero (predose) to fixed time-point 336 h (2 weeks) after the end of infusion
CDAI: Crohn's disease activity index
CL: total clearance
CRP: C-reactive protein
$C_{max}$: maximum serum concentration
ELISA: enzyme-linked immunosorbant assay
FKN: fractalkine
IgG: immunoglobulin G
NONMEN: nonlinear mixed effect model
SAS: statistical analysis system
$t_{1/2}$: serum elimination half-life
$t_{max}$: time to reach peak serum concentration
$V_d$: volume of distribution

EXAMPLES

Example 1: Preparation of Humanized Anti-Human Fractalkine Antibody

In the following administration study in a human, a humanized anti-human fractalkine antibody H3-2L4 was used. Preparation of H3-2L4, which included humanization, was carried out in the same manner as that described in WO2011/052799. H3-2L4 used in Example 2 and the subsequent examples was prepared by the method described in the following 1-1. and 1-2.

1-1. Expression Vector

An expression vector for the humanized anti-human fractalkine antibody (H3-2L4) was produced as follows.

First, a signal sequence (SEQ ID NO: 3) was added to the N-terminus of the amino acid sequence (SEQ ID NO: 1) of a heavy chain variable region (H3-2) of the humanized anti-human fractalkine antibody (H3-2L4), and the amino acid sequence (SEQ ID NO: 4) of the constant region of human IgG2, into which two mutations (V234A and G237A) had been inserted, was added to the C-terminus thereof (SEQ ID NO: 5). Subsequently, a signal sequence (SEQ ID NO: 6) was added to the N-terminus of the amino acid sequence (SEQ ID NO: 2) of a light chain variable region (L4) of the humanized anti-human fractalkine antibody (H3-2L4), and the amino acid sequence (SEQ ID NO: 7) of the constant region of human Igκ was added to the C-terminus thereof (SEQ ID NO: 8). In order to allow these amino acid sequences (SEQ ID NOS: 5 and 8) to express in CHO cells, they were converted to optimal gene sequences. To the 5'-terminus of each gene sequence, a recognition sequence of the restriction enzyme HindIII and a Kozak sequence were added, and to the 3'-terminus thereof, a stop codon and a recognition sequence of the restriction enzyme EcoRI were added, so that the sequences were totally synthesized (SEQ ID NOS: 9 and 10).

It is to be noted that the sequences specified with SEQ ID NOS: 1 to 10 are as follows.

Amino acid sequence (SEQ ID NO: 1) of a heavy chain variable region (H3-2)
QVQLVQSGAEVKKPGASVKVSCKASGYTFTNYYIHWVKQAPGQGLEWIGW

IYPGDGSPKFNERFKGRTTLTADKSTNTAYMLLSSLRSEDTAVYFCATGP

TDGDYFDYWGQGTTVTVSS

Amino acid sequence (SEQ ID NO: 2) of a light chain variable region (L4)
DIQMTQSPSSLSASVGDRVTITCRASGNIHNFLAWYQQKPGKAPKLLIYN

EKTLADGVPSRFSGSGSGTDYTLTISSLQPEDFATYFCQQFWSTPYTFGG

GTKVEIK

Signal sequence (SEQ ID NO: 3)
MEWSWVFLFFLSVTTGVHS

Amino acid sequence (SEQ ID NO: 4) of the constant region of human IgG2, into which two mutations (V234A and G237A) had been inserted
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPAAAPSVFLFPPKPKDTLMISRTPEVTCVVVDVSHEDP
EVQFNWYVDGVEVHNAKTKPREEQFNSTFRVVSVLTVVHQDWLNGKEYKC
KVSNKGLPAPIEKTISKTKGQPREPQVYTLPPSREEMTKNQVSLTCLVKG
FYPSDIAVEWESNGQPENNYKTTPPMLDSDGSFFLYSKLTVDKSRWQQGN
VFSCSVMHEALHNHYTQKSLSLSPGK (SEQ ID NO: 5)
MEWSWVFLFFLSVTTGVHSQVQLVQSGAEVKKPGASVKVSCKASGYTFTN
YYIHWVKQAPGQGLEWIGWIYPGDSPKFNERFKGRTTLTADKSTNTAYM
LLSSLRSEDTAVYFCATGPTDGDYFDYWGQGTTVTVSSASTKGPSVFPLA
PCSRSTSESTAALGCLVKDYFPEPVTVSWNSGALTSGVHTFPAVLQSSGL
YSLSSVVTVPSSNFGTQTYTCNVDHKPSNTKVDKTVERKCCVECPPCPAP
PAAAPSVFLFPPKPKDTLMISRTPEVTCVVVDVSHEDPEVQFNWYVDGVE
VHNAKTKPREEQFNSTFRVVSVLTVVHQDWLNGKEYKCKVSNKGLPAPIE
KTISKTKGQPREPQVYTLPPSREEMTKNQVSLTCLVKGFYPSDIAVEWES
NGQPENNYKTTPPMLDSDGSFFLYSKLTVDKSRWQQGNVFSCSVMHEALH
NHYTQKSLSLSPGK

Signal sequence (SEQ ID NO: 6)
MSVPTQVLGLLLLWLTDARC

Amino acid sequence (SEQ ID NO: 7) of the
constant region of human IgK
RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC (SEQ ID NO: 8)
MSVPTQVLGLLLLWLTDARCDIQMTQSPSSLSASVGDRVTITCRASGNIH
NFLAWYQQKPGKAPKLLIYNEKTLADGVPSRFSGSGSGTDYTLTISSLQP
EDFATYFCQQFWSTPYTFGGGTKVEIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC (SEQ ID NO: 9)
AAGCTTGCCGCCACCATGGAATGGTCCTGGGTGTTCCTGTTCTTCCTGTC
CGTGACCACCGGCGTGCACTCCCAGGTGCAGCTGGTGCAGTCTGGCGCCG
AAGTGAAGAAACCTGGCGCCTCCGTGAAGGTGTCCTGCAAGGCCTCCGGC
TACACCTTCACCAACTACTACATCCACTGGGTGAAACAGGCCCCAGGACA
GGGCCTGGAATGGATCGGCTGGATCTACCCCGGCGACGGCTCCCCCAAGT
TCAACGAGCGGTTCAAGGGCCGGACCACCCTGACCGCCGACAAGTCCACC
AACACCGCCTACATGCTGCTGTCCTCCCTGCGGAGCGAGGATACCGCCGT
GTACTTCTGCGCCACCGGCCCTACCGACGGCGACTACTTCGACTACTGGG
GCCAGGGCACCACCGTGACCGTGTCCTCTGCCTCCACCAAGGGCCCCTCC
GTGTTCCCTCTGGCCCCTTGCTCCCGGTCCACCTCTGAGTCTACCGCCGC
TCTGGGCTGCCTGGTCAAAGACTACTTCCCCGAGCCTGTGACAGTGTCCT
GGAACTCTGGCGCCCTGACCTCTGGAGTGCATACCTTCCCTGCCGTGCTG
CAGTCATCCGGCCTGTACTCCCTGTCCTCCGTGGTGACAGTGCCCTCCTC
CAACTTCGGCACCCAGACCTACACCTGTAACGTGGACCACAAGCCCTCCA
ACACCAAGGTGGACAAGACCGTGGAACGGAAGTGCTGCGTGGAATGCCCC
CCCTGTCCTGCCCCTCCTGCCGCCGCTCCTTCCGTGTTTCTGTTCCCCCC
AAAGCCCAAGGACACCCTGATGATCTCCCGGACCCCCGAAGTGACCTGCG
TGGTGGTGGACGTGTCCCACGAGGACCCCGAGGTGCAGTTCAATTGGTAC
GTGGACGGCGTGGAAGTGCACAACGCCAAGACCAAGCCCAGAGAGGAACA
GTTCAACTCCACCTTCCGGGTGGTGTCCGTGCTGACCGTGGTGCACCAGG
ACTGGCTGAACGGCAAAGAGTACAAGTGCAAGGTCTCCAACAAGGGCCTG
CCTGCCCCCATCGAAAAGACCATCAGCAAGACCAAGGGCCAGCCCCGCGA
GCCCCAGGTGTACACACTGCCCCCCAGCCGGGAAGAGATGACCAAGAACC
AGGTGTCCCTGACCTGTCTGGTGAAAGGCTTCTACCCCTCCGATATCGCC
GTGGAATGGGAGTCCAACGGACAGCCCGAGAACAACTACAAGACCACCCC
CCCCATGCTGGACTCCGACGGCTCATTCTTCCTGTACTCCAAGCTGACAG
TGGACAAGTCCCGGTGGCAGCAGGGCAACGTGTTCTCCTGCAGCGTGATG
CACGAGGCCCTGCACAACCACTACACCCAGAAGTCCCTGAGCCTGAGCCC
CGGCAAGTGATGAATTC (SEQ ID NO: 10)
AAGCTTGCCGCCACCATGTCCGTGCCCACCCAGGTGCTGGGCCTGCTGCT
GCTGTGGCTGACCGACGCCAGATGCGACATCCAGATGACCCAGTCCCCCT
CCAGCCTGTCCGCCTCTGTGGGCGACAGAGTGACCATCACCTGTCGGGCC
TCCGGCAACATCCACAACTTTCTGGCCTGGTATCAGCAGAAGCCCGGCAA
GGCCCCCAAGCTGCTGATCTACAACGAAAAGACCCTGGCCGACGGCGTGC
CCTCCAGATTCTCCGGCTCTGGCTCCGGCACCGACTACACCCTGACCATC
TCCAGCCTGCAGCCCGAGGACTTCGCCACCTACTTTTGCCAGCAGTTCTG
GTCCACCCCCTACACCTTCGGCGGAGGCACCAAGGTGGAAATCAAGCGGA
CCGTGGCCGCTCCCTCCGTGTTCATCTTCCCACCCTCCGACGAGCAGCTG
AAGTCCGGCACCGCCTCCGTGGTGTGCCTGCTGAACAACTTCTACCCCCG
CGAGGCCAAGGTGCAGTGGAAGGTGGACAACGCCCTGCAGTCCGGCAACT
CCCAGGAATCCGTCACCGAGCAGGACTCCAAGGACAGCACCTACTCCCTG
TCCTCCACCCTGACCCTGTCCAAGGCCGACTACGAGAAGCACAAGGTGTA
CGCCTGCGAAGTGACCCACCAGGGCCTGTCCAGCCCCGTGACCAAGTCCT
TCAACCGGGGCGAGTGCTGATGAATTC The totally synthesized gene sequence encoding a heavy chain was cleaved with the restriction enzymes HindIII and EcoRI, and it was then inserted into the HindIII-EcoRI site of a pEE6.4 vector (Lonza). The totally synthesized gene sequence encoding a light chain was cleaved with the restriction enzymes HindIII and EcoRI, and it was then inserted into the HindIII-EcoRI site of a pEE12.4 vector (Lonza). The two vectors were each cleaved with the restriction enzymes NotI and PvuI, and vector fragments each containing a heavy chain or a light chain were ligated to each other to construct an expression vector.

1-2. Construction of Cell Line Expressing Antibody H3-2L4, and Obtainment of Antibody H3-2L4

The constructed expression vector was introduced by electroporation into CHOK1SV cells (Lonza) conditioned in a medium of CD-CHO/6 mM L-glutamine. After completion of the gene introduction, selection was carried out in a medium of CD-CHO/50 uM MSX under an environment of 37° C./10% $CO_2$, to obtain cells expressing an antibody of interest. Thereafter, the cells were cloned to produce a cell bank. The produced cell bank was revived and cultured, and a culture supernatant was then purified by chromatography to obtain the antibody H3-2L4 of interest.

The antibody H3-2L4 obtained as described above had a heavy chain and a light chain having the amino acid sequences shown in SEQ ID NOS: 11 and 12, respectively.

```
Full-length heavy chain of H3-2L4
                                   (SEQ ID NO: 11)
QVQLVQSGAEVKKPGASVKVSCKASGYTFTNYYIHWVKQAPGQGLEWIGW

IYPGDGSPKFNERFKGRTTLTADKSTNTAYMLLSSLRSEDTAVYFCATGP

TDGDYFDYWGQGTTVTVSSASTKGPSVFPLAPCSRSTSESTAALGCLVKD

YFPEPVTVSWNSGALTSGVHTFPAVLQSSGLYSLSSVVTVPSSNFGTQTY

TCNVDHKPSNTKVDKTVERKCCVECPPCPAPPAAAPSVFLFPPKPKDTLM

ISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLP

PSREEMTKNQVSLTCLVKGFYPSDIAVEWESNGQPENNYKTTPPMLDSDG

SFFLYSKLTVDKSRWQQGNVFSCSVMHEALHNHYTQKSLSLSPGK

Full-length light chain of H3-2L4
                                   (SEQ ID NO: 12)
DIQMTQSPSSLSASVGDRVTITCRASGNIHNFLAWYQQKPGKAPKLLIYN

EKTLADGVPSRFSGSGSGTDYTLTISSLQPEDFATYFCQQFWSTPYTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

Moreover, the amino acid sequences of the heavy chain variable region and the light chain variable region of the antibody H3-2L4 are as follows:

```
Heavy chain variable region of H3-2L4
                                   (SEQ ID NO: 13)
QVQLVQSGAEVKKPGASVKVSCKASGYTFTNYYIHWVKQAPGQGLEWIGW

IYPGDGSPKFNERFKGRTTLTADKSTNTAYMLLSSLRSEDTAVYFCATGP

TDGDYFDYWGQGTTVTVSS

Light chain variable region of H3-2L4
                                   (SEQ ID NO: 14)
DIQMTQSPSSLSASVGDRVTITCRASGNIHNFLAWYQQKPGKAPKLLIYN

EKTLADGVPSRFSGSGSGTDYTLTISSLQPEDFATYFCQQFWSTPYTFGG

GTKVEIK
```

Furthermore, the amino acid sequences of the CDR-H1 to CDR-H3 and the CDR-L1 to CDR-L3 of the antibody H3-2L4 are as follows:

```
CDR-H1 of H3-2L4
                                   (SEQ ID NO: 15)
NYYIH

CDR-H2 of H3-2L4
                                   (SEQ ID NO: 16)
WIYPGDGSPKFNERFKG

CDR-H3 of H3-2L4
                                   (SEQ ID NO: 17)
GPTDGDYFDY

CDR-L1 of H3-2L4
                                   (SEQ ID NO: 18)
RASGNIHNFLA

CDR-L2 of H3-2L4
                                   (SEQ ID NO: 19)
NEKTLAD

CDR-L3 of H3-2L4
                                   (SEQ ID NO: 20)
QQFWSTPYT
```

Example 2: Single-Dose Administration Study

Healthy adult male subjects were used, and a phase I trial was carried out to evaluate safety, tolerability, and pharmacokinetics, when H3-2L4 was administered to the subjects by single-dose intravenous administration.

2-1. [Trial Design]

The present trial was a single dose escalation study involving single institution, randomization, double blind and placebo control, which was carried out for the main purpose of evaluating safety and tolerability when H3-2L4 was administered to Japanese healthy adult male subjects by single-dose intravenous administration. In the present trial, 64 subjects were divided into 8 cohorts (0.0006, 0.006, 0.04, 0.2, 1, 3, 6, and 10 mg/kg groups), and thereafter, by single-dose intravenous administration, 6 subjects in each of the 8 cohorts were administered with H3-2L4, and 2 subjects therein were administered with a placebo.

The present trial was constituted with a screening period, an observation hospitalization period, an administration hospitalization period (double blind trial), a follow-up phase 1 period (double blind trial), and a follow-up phase 2 period (established for only Cohorts 5 to 8: non-blinded trial).

Within a period from 27 days to 2 days before administration of a trial drug, a screening test was carried out, and one day before the drug administration, a test performed in an observation hospitalization period was carried out, so as to confirm eligibility. Subjects whose eligibility had been confirmed were randomly assigned to an H3-2L4 group or a placebo group, based on an assignment list prepared by an assignment officer. With regard to two subjects in each cohort on day 1, one subject was assigned to H3-2L4 administration, and the other subject was assigned to placebo administration, followed by administration. The remaining six subjects were assigned to five H3-2L4 administration subjects and one placebo administration subject, and administration was carried out from day 2 to day 4. The number of subjects to which the drug was administered on the same day was set at 2, and two or more hours after initiation of the administration to one subject, the administration was carried out to the other subject. The trial drug was administered to the subjects by dissolving H3-2L4 or the placebo in a normal saline, and then administering the obtained solution to the subjects for approximately 30 minutes by intravenous drip infusion. The present trial was carried out by a single-dose administration, and administration to the subjects was carried out only once, regardless of their mealtime.

For one week after completion of the administration, the subjects were observed and inspected in the hospital, and thereafter, in the outpatient service, Cohorts 1 to 4 (0.0006, 0.006, and 0.04 mg/kg groups) were observed and inspected until 8 weeks after completion of the administration, and Cohorts 5 to 8 (0.2, 1, 3, 6, and 10 mg/kg groups) were observed and inspected until 24 weeks after completion of the administration.

Cohort migration was carried out based on the results of safety obtained from each cohort, when both a trial investigator and a trial client (a representative from a medical expert, a person in charge of safety department for trial clients, and a trial client) judged that there would be no problems regarding cohort migration. In principle, such cohort migration was carried out at an interval of 3 weeks after completion of the administration to the first subject in the previous cohort.

The types of the trial drugs used in the present study were as follows.

TABLE 1

Types of trial drugs

| Type | Dosage form and content | Manufacturer |
|---|---|---|
| H3-2L4 | Aqueous solution containing 100 mg of H3-2L4 in 1 vial (10 mL) | Eisai Co., Ltd. |
| Placebo | Aqueous solution not containing H3-2L4 in 1 vial (10 mL) | | intravenous drip infusion using an in-line filter (pore diameter: 0.2 μm) for approximately 30 minutes (including normal saline flushing).

TABLE 2

Amounts of liquids administered and types of pumps

| Cohort | Trial drug | | Amount of liquid administered | Pump |
|---|---|---|---|---|
| 1 | H3-2L4 | 0.0006 mg/kg or placebo | 10 mL | Syringe pump |
| 2 | H3-2L4 | 0.006 mg/kg or placebo | 100 mL | Infusion pump |
| 3 | H3-2L4 | 0.04 mg/kg or placebo | | |
| 4 | H3-2L4 | 0.2 mg/kg or placebo | | |
| 5 | H3-2L4 | 1 mg/kg or placebo | | |
| 6 | H3-2L4 | 3 mg/kg or placebo | | |
| 7 | H3-2L4 | 6 mg/kg or placebo | | |
| 8 | H3-2L4 | 10 mg/kg or placebo | | |

2-3. [Analysis of Serum Concentration of H3-2L4]

The serum concentration of H3-2L4 was measured by a validated measurement method. Specifically, H3-2L4 in serum was allowed to bind to human fractalkine that was solid-phased on a microplate, and a ruthenium-labeled anti-H3-2L4 rabbit polyclonal antibody was then allowed to react therewith. Thereafter, the amount of electrochemical luminescence was measured using Sector Imager 6000 (Meso Scale Discovery) to quantify the serum concentration of H3-2L4. Blood to be used to measure the serum concentration of H3-2L4 was collected in blood collection timing shown in the following Table 3.

TABLE 3

Blood collection timing for evaluation of pharmacokinetics

| Period | Blood collection timing (time elapsed after completion of administration on day 1) | | Permissible range of blood collection time |
|---|---|---|---|
| Day 1 | Immediately before administration at the completion of administration (0 hours) | | −3 hours |
| | | | +5 minutes |
| | 1 hour | | ±5 minutes |
| | 2 hours | | |
| | 6 hours | | |
| | 12 hours | | |
| Day 2 | 24 hours | Same time as end time of administration on day 1 | ±1 hour |
| Day 3 | 48 hours | | |
| Day 5 | 96 hours | | |
| Day 8 | 168 hours | | |
| Day 15 | 336 hours | 2 weeks after Same time as end time of administration on day 1 on same day of week as day 1 | ±24 hours |
| Day 22 | 504 hours | 3 weeks after | |
| Day 29 | 672 hours | 4 weeks after | |
| Day 36 | 840 hours | 5 weeks after | |
| Day 43 | 1008 hours | 6 weeks after | |
| Day 57 | 1344 hours | 8 weeks after | |
| Day 71 | 1680 hours | 10 weeks after | ±72 hours |
| Day 85 | 2016 hours | 12 weeks after | |
| Day 99 | 2352 hours | 14 weeks after | |
| Day 113 | 2688 hours | 16 weeks after | |
| Day 127 | 3024 hours | 18 weeks after | |
| Day 141 | 3360 hours | 20 weeks after | |
| Day 155 | 3696 hours | 22 weeks after | |
| Day 169 | 4032 hours | 24 weeks after | |

2-2. [Administration of Trial Drugs]

H3-2L4 or placebo was diluted with a normal saline, depending on the body weight of each subject to adjust the amounts of liquids administered as shown in Table 2. Upon administration, employing a syringe pump or an infusion pump, each solution was administered to the subjects by 2-4. [Analysis of Pharmacokinetics]

Pharmacokinetics were analyzed based on the data regarding the serum concentration of H3-2L4, using a population of subjects having data from which one or more pharmacokinetic parameters can be calculated (hereinafter referred to as a "pharmacokinetics analysis target population"). In the present trial, with regard to 16 subjects to which placebo had been administered, 6 subjects to which 0.0006 mg/kg H3-2L4 had been administered, and 6 subjects to which 0.006 mg/kg H3-2L4 had been administered, the serum concentration of H3-2L4 of each subject was less than the lower quantification limit value (0.100 μg/mL). Accordingly, 36 subjects excluding the aforementioned subjects were determined to be a pharmacokinetics analysis target population. The summary statistics of the serum concentration of H3-2L4 was calculated for individual dosages in predetermined periods. A transition diagram of the serum concentration of H3-2L4 was prepared, and then, pharmacokinetic parameters including $C_{max}$, $t_{max}$, $AUC_{(0-t)}$, $AUC_{(0-inf)}$, $t_{1/2}$, CL and $V_d$ were calculated by a non-compartment analysis, using the serum concentration of H3-2L4. In addition, using the obtained $C_{max}$, $AUC_{(0-t)}$ and $AUC_{(0-inf)}$, dose proportionality was analyzed. The analysis was carried out using SAS, WinNonlin, Pharsight Knowledgebase Server, Microsoft Excel, and S-PLUS.

The thus calculated results are shown in the following Table 4 and FIG. 1. It is to be noted that the mean values of the pharmacokinetic parameters shown in Table 4, except for the $t_{max}$, are shown in the form of arithmetical mean values.

TABLE 4

Summary of pharmacokinetic parameters upon single-dose intravenous administration of H3-2L4 to healthy adults

| Pharmacokinetic parameters | Summary statistics | Dose | | | | | |
|---|---|---|---|---|---|---|---|
| | | 0.04 mg/kg | 0.2 mg/kg | 1 mg/kg | 3 mg/kg | 6 mg/kg | 10 mg/kg |
| $C_{max}$ (μg/mL) | Number of subjects | 6 | 6 | 6 | 6 | 6 | 6 |
| | Mean value | 0.860 | 4.92 | 23.5 | 69.8 | 127 | 238 |
| | Standard deviation | 0.0925 | 0.375 | 2.43 | 4.53 | 8.67 | 18.1 |
| | Mean value/Dose | 21.5 | 24.6 | 23.5 | 23.3 | 21.2 | 23.8 |
| $t_{max}$ (h) | Number of subjects | 6 | 6 | 6 | 6 | 6 | 6 |
| | Median | 0.500 | 0.500 | 0.500 | 1.000 | 1.500 | 0.500 |
| | Minimum value | 0.50 | 0.50 | 0.50 | 0.50 | 0.50 | 0.50 |
| | Maximum value | 0.50 | 1.50 | 1.50 | 6.50 | 6.50 | 1.50 |
| $AUC_{(0-t)}$ (μg·h/mL) | Number of subjects | 6 | 6 | 6 | 6 | 6 | 6 |
| | Mean value | 7.04 | 202 | 2520 | 13700 | 35200 | 69500 |
| | Standard deviation | 1.89 | 16.4 | 300 | 1560 | 3170 | 10400 |
| $AUC_{(0-336\ h)}$ (μg·h/mL) | Number of subjects | 6 | 6 | 6 | 6 | 6 | 6 |
| | Mean value | — | — | 2520 | 10400 | 20300 | 37700 |
| | Standard deviation | — | — | 300 | 905 | 1250 | 3780 |
| $t_{1/2,\ \beta}$ (h) | Number of subjects | — | — | 6 | 6 | 6 | 6 |
| | Mean value | — | — | 122 | 224 | 346 | 353 |
| | Standard deviation | — | — | 8.78 | 29.9 | 32.8 | 62.6 |
| $t_{1/2,\ \gamma}$ (h) | Number of subjects | 6 | 6 | — | — | — | — |
| | Mean value | 8.55 | 30.3 | — | — | — | — |
| | Standard deviation | 0.705 | 7.66 | — | — | — | — |

As a result of the analysis, it was considered that the pharmacokinetics obtained by single-dose intravenous administration of H3-2L4 would show a three-phase profile consisting of phase α, phase μ and phase γ in 0.04 to 10 mg/kg. After completion of the intravenous drip infusion, an initial distribution phase that was promptly reduced from the $C_{max}$ (phase α) was present, and thereafter, a slowly disappearing phase (phase β) was observed in a high concentration, and a rapid final disappearing phase (phase γ) was observed in a low concentration. The boundary point between the phase γ and the phase β was assumed to be around 10 μg/mL. In the 0.04 and 0.2 mg/kg groups, a two-phase profile was found, and it was considered that the phase γ would appear following the phase α. In the 1 to 10 mg/kg groups, since the number of collected blood samples necessary for precise evaluation of the phase γ as a finally disappearing phase was insufficient, phase γ-dependent pharmacokinetic parameters could not be calculated. After completion of the intravenous drip infusion for 30 minutes, almost all of the subjects reached the $t_{max}$ after 0.5 hours, but some subjects reached the $t_{max}$ after 6.5 hours. The $t_{1/2},\beta$ was longer than the $t_{1/2},\gamma$ and it was prolonged with an increase in the dose, but the $t_{1/2},\beta$ in the 6 and 10 mg/kg groups became almost the same, and thus, it was considered that it would reach a plateau. The $C_{max}$ was increased in proportion to the dose in 0.04 to 10 mg/kg groups. However, the $AUC_{(0-t)}$ and $AUC_{(0-inf)}$ were not in proportion to the dose, and H3-2L4 showed non-linear pharmacokinetics.

Example 3: Multiple-Dose Administration Study

A phase I/II clinical study was carried out by repeated intravenous administration of H3-2L4 to Crohn's disease patients used as subjects, so as to evaluate safety, tolerability, pharmacokinetics, and efficacy on Crohn's disease.
3-1. [Trial Design]

The present trial was a multiple ascending dose (MAD) study involving multi-institutional joint, non-blind and non-control, which was carried out for the main purpose of evaluating safety and tolerability when H3-2L4 was administered to Japanese Crohn's disease patients used as subjects by repeated intravenous administration. In the present trial, randomization was not carried out. In the present trial, 21 subjects were divided by 6 subjects, 8 subjects, and 7 subjects into Cohorts 1 to 3 (2, 5, and 10 mg/kg groups), respectively. Thereafter, H3-2L4 was administered to the subjects by repeated intravenous administration. Moreover, regarding Cohort 4 (15 mg/kg group), H3-2L4 was administered to at least 6 subjects by repeated intravenous administration.

The present trial was constituted with a screening period, an observation period, an administration period, a continuous administration period, and a follow-up period.

A screening test was carried out within 42 to 2 days before initiation of the administration of the trial drug, and an observation period test was carried out one day before initial administration of the trial drug or before the administration on the administration day. To subjects who were confirmed to have eligibility, H3-2L4 was administered.

Selection criteria for eligibility were as follows:
(1) Patients who are 20 years old or older and younger than 65 years old;
(2) Patients who are diagnosed to have Crohn's disease in accordance with the Crohn's disease diagnosis criteria (2012) by the "Research Study regarding Refractory Inflammatory Bowel Disease" Team, Health Labour Sciences Research Grant Study for Refractory Diseases;
(3) Patients whose severity in the observation period is a mild to medium degree (CDAI is 150 or more and less than 450, based on the Crohn's disease diagnosis criteria); and
(4) Patients who were administered with a 5-aminosalicylic acid (5-ASA) formulation, salazosulfapyridine, adrenocorticosteroid, an immunomodulator, infliximab (including biosimilars, and so on) or adalimumab in the past, and were not found to have effects, or patients who were found to have effects, but after that, the effects were attenuated or disappeared, or patients to which administration could not be continued due to side effects (except for infliximab and adalimumab).

H3-2L4 was dissolved in approximately 100 mL of normal saline, and was then administered to the patients for approximately 30 minutes by intravenous drip infusion. In the administration period, with regard to Cohort 1 (2 mg/kg) and Cohort 2 (5 mg/kg), H3-2L4 was administered to the patients every two weeks until 10 weeks in a total of 6 times (two times amount in 0 week), and with regard to Cohort 3 (10 mg/kg) and Cohort 4 (15 mg/kg), H3-2L4 was administered to the patients at the 0th week, 1st week, 2nd week, and then every two weeks until the 10th week in total of 7 times. In the evaluation carried out at the 12th week, the subjects who had no problems regarding safety, had a Crohn's disease activity index (CDAI) of less than 150 or a reduction in the CDAI from the observation period that is 70 or more, and wanted continuous administration, were further administered with H3-2L4 at the same dose as described above, every two weeks, 20 times (40 weeks) (continuous administration period). Regarding the continuous administration period, the administration could be changed (reduced) to administration at the same dose as described above every four weeks according to the judgement of a trial investigator or a doctor in charge of the trial (wherein it is also possible to return the administration to an administration every two weeks).

Cohort migration was carried out based on the results of safety obtained from each cohort, when both a trial investigator and a trial client judged that there would be no problems regarding cohort migration.

The type of the trial drug used in the present study was as follows.

TABLE 5

| Trial drug | | |
|---|---|---|
| Type | Dosage form and content | Manufacturer |
| H3-2L4 | Aqueous solution containing 100 mg of H3-2L4 in 1 vial (1 mL) | Eisai Co., Ltd. |

3-2. [Administration of Trial Drug]

H3-2L4 was diluted with a normal saline, depending on the body weight of each subject, so as to adjust the administered amount of a liquid containing each dose of H3-2L4 (approximately 100 mL). Individual doses (2, 5, 10 and 15 mg/kg) and the administration method are as shown in Table 6. The body weight used to calculate the dose (total amount) relative to body weight was measured in the observation period, the 12th week, the 24th week, and the 36th week, and even if the body weight was increased or decreased during other periods, the relative dose (total amount) was not changed. Upon administration, employing an infusion pump, each solution was administered to the subjects by intravenous drip infusion using an in-line filter (pore diameter: 0.2 μm) for approximately 30 minutes (including normal saline flushing). It is to be noted that the trial drug could be administered regardless of their mealtime.

TABLE 6

Dose of H3-2L4 and administration method

| Cohort | Trial drug | | Amount of liquid administered | Pump |
|---|---|---|---|---|
| 1 | H3-2L4 | 2 mg/kg | Approx. 100 mL | Infusion pump |
| 2 | H3-2L4 | 5 mg/kg | | |
| 3 | H3-2L4 | 10 mg/kg | | |
| 4 | H3-2L4 | 15 mg/kg | | |

3-3. [Pharmacokinetics and Pharmacodynamics]

The serum concentration of H3-2L4 and the serum concentration of total FKN were measured by validated measurement methods. The serum concentration of H3-2L4 was measured by the method described in 2-4 of Example 2. The serum concentration of total FKN was measured by the sandwich ELISA method described in WO2011/052799, involving sandwiching with two types of anti-human fractalkine monoclonal antibodies 1F3 and 3A5-2. Specifically, total FKN in the serum was captured by 1F3 that was solid-phased on a plate, it was then sandwiched with 3A5-2 labeled with horse radish peroxidase (HRP), it was further reacted with 3,3',5,5'-tetramethylbenzidine (TMB) as a substrate of HRP, and the coloration value was then measured using an auto-reader (Microplate reader Envision, Perkin Elmer Japan), so that the serum concentration of total FKN was quantified.

Pharmacokinetics were analyzed based on the data of the serum concentration of H3-2L4, using a population of subjects who were administered with the trial drug, and as a result, had one or more of serum H3-2L4 concentration data to be evaluated (hereinafter referred to as a "pharmacokinetics analysis target population"). The summary statistics of the serum concentration of H3-2L4 was calculated for individual dosages in predetermined periods, and a transition diagram of the serum concentration of H3-2L4 was prepared.

Pharmacodynamics were analyzed using a population of subjects who were administered with the trial drug, and as a result, had one or more of pharmacodynamic biomarker data to be evaluated (hereinafter referred to as a "pharmacodynamics analysis target population"). With regard to the measurement values of the serum concentration of total FKN, the summary statistics was calculated for individual dosages in predetermined evaluation periods.

3-3-1. [Serum Concentration of H3-2L4 and Serum Concentration of Total FKN]

From the time of administration of the trial drug until the 12th week, blood was collected to measure the serum concentration of H3-2L4 and the serum concentration of total FKN, within 10 minutes before and after administration (0 hour), in the periods indicated with the letters X, shown in the timeline of Table 7 for Cohorts 1 and 2, and of Table 8 for Cohorts 3 and 4. With regard to the subjects who were migrated in the continuous administration period, blood was further collected every four weeks until the 52nd week. Moreover, the subjects, who were withdrawn from the trial during the administration period or the continuous administration period, were subjected to blood collection at the time of withdrawal.

TABLE 7

Timeline for Cohorts 1 and 2

| | Period after administration | | Evaluation item | | | | |
|---|---|---|---|---|---|---|---|
| | | | Administration of trial drug | CDAI | CRP | Serum concentration of H3-2L4 | Serum concentration of total FKN |
| Screening period | −41 to −1 days | | | | X | | |
| Observation period | 0 days | | | X | X | | |
| | 1 day | Before administration | | | | X | X |
| Administration period | | During administration | X | | | | |
| | | 0 h | | | | X | X |
| | | 2-6 h | | | X | | |
| | 2 days | 16 or more hours after administration | | | X | X | X |
| | 15 ± 3 days | Before administration | | X | X | X | X |
| | | During administration | X | | | | |
| | | 0 h | | | | X | X |
| | | 2-6 h | | | X | | |
| | 16 ± 3 days | 16 or more hours after administration | | | | | |
| | 4 weeks ± 3 days | | X | X | X | X | X |
| | 6 weeks ± 3 days | | X | | | X | X |
| | 8 weeks ± 3 days | | X | X | X | X | X |
| | 10 weeks ± 3 days | | X | | | X | X |
| | 12 weeks ± 3 days | | X | X | X | X | X |
| Continuous administration period | 14 weeks ± 7 days | | (X) | | | | |
| | 16 weeks ± 7 days | | X | X | X | X | X |
| | 18 weeks ± 7 days | | (X) | | | | |
| | 20 weeks ± 7 days | | X | X | X | X | X |
| | 22 weeks ± 7 days | | (X) | | | | |
| | 24 weeks ± 7 days | | X | X | X | X | X |

TABLE 7-continued

Timeline for Cohorts 1 and 2

|  | Period after administration | Administration of trial drug | CDAI | CRP | Serum concentration of H3-2L4 | Serum concentration of total FKN |
|---|---|---|---|---|---|---|
|  | 26 weeks ± 7 days | (X) |  |  |  |  |
|  | 28 weeks ± 7 days | X | X | X | X | X |
|  | 30 weeks ± 7 days | (X) |  |  |  |  |
|  | 32 weeks ± 7 days | X | X | X | X | X |
|  | 34 weeks ± 7 days | (X) |  |  |  |  |
|  | 36 weeks ± 7 days | X | X | X | X | X |
|  | 38 weeks ± 7 days | (X) |  |  |  |  |
|  | 40 weeks ± 7 days | X | X | X | X | X |
|  | 42 weeks ± 7 days | (X) |  |  |  |  |
|  | 44 weeks ± 7 days | X | X | X | X | X |
|  | 46 weeks ± 7 days | (X) |  |  |  |  |
|  | 48 weeks ± 7 days | X | X | X | X | X |
|  | 50 weeks ± 7 days | (X) |  |  |  |  |
|  | 52 weeks ± 7 days |  | X | X | X | X |
| Administration period/continuous administration period | Upon termination |  | X | X | X | X |
| Follow-up period | 28 days after completion or termination |  |  | X |  |  |
|  | 70 days after final administration |  |  |  |  |  |

TABLE 8

Timeline for Cohorts 3 and 4

|  | Period after administration | | Administration of trial drug | CDAI | CRP | Serum concentration of H3-2L4 | Serum concentration of total FKN |
|---|---|---|---|---|---|---|---|
| Screening period | −41 to −1 days | |  |  | X |  |  |
| Observation period | 0 days | |  | X | X |  |  |
| Administration period | 1 day | Before administration |  |  |  | X | X |
|  |  | During administration 0 h | X |  |  | X | X |
|  |  | 2-6 h |  |  | X |  |  |
|  | 2 days | 16 or more hours after administration |  |  | X | X | X |
|  | 8 ± 3 days | Before administration |  |  | X | X | X |
|  |  | During administration 0 h | X |  |  | X | X |
|  |  | 2-6 h |  |  | X |  |  |
|  | 9 ± 3 days | 16 or more hours after administration |  |  |  |  |  |
|  | 2 weeks ± 3 days | | X | X | X | X | X |
|  | 4 weeks ± 3 days | | X | X | X | X | X |
|  | 6 weeks ± 3 days | | X |  |  | X | X |
|  | 8 weeks ± 3 days | | X | X | X | X | X |
|  | 10 weeks ± 3 days | | X |  |  | X | X |
|  | 12 weeks ± 3 days | | X | X | X | X | X |
| Continuous administration period | 14 weeks ± 7 days | | (X) |  |  |  |  |
|  | 16 weeks ± 7 days | | X | X | X | X | X |
|  | 18 weeks ± 7 days | | (X) |  |  |  |  |
|  | 20 weeks ± 7 days | | X | X | X | X | X |
|  | 22 weeks ± 7 days | | (X) |  |  |  |  |
|  | 24 weeks ± 7 days | | X | X | X | X | X |
|  | 26 weeks ± 7 days | | (X) |  |  |  |  |
|  | 28 weeks ± 7 days | | X | X | X | X | X |
|  | 30 weeks ± 7 days | | (X) |  |  |  |  |
|  | 32 weeks ± 7 days | | X | X | X | X | X |
|  | 34 weeks ± 7 days | | (X) |  |  |  |  |
|  | 36 weeks ± 7 days | | X | X | X | X | X |
|  | 38 weeks ± 7 days | | (X) |  |  |  |  |
|  | 40 weeks ± 7 days | | X | X | X | X | X |
|  | 42 weeks ± 7 days | | (X) |  |  |  |  |
|  | 44 weeks ± 7 days | | X | X | X | X | X |
|  | 46 weeks ± 7 days | | (X) |  |  |  |  |

TABLE 8-continued

Timeline for Cohorts 3 and 4

|  | Period after administration | Evaluation item | | | | |
|---|---|---|---|---|---|---|
|  |  | Administration of trial drug | CDAI | CRP | Serum concentration of H3-2L4 | Serum concentration of total FKN |
| Administration period/continuous administration period | 48 weeks ± 7 days | X | X | X | X | X |
|  | 50 weeks ± 7 days | (X) | | | | |
|  | 52 weeks ± 7 days | | X | X | X | X |
|  | Upon termination | | X | X | X | X |
| Follow-up period | 28 days after completion or termination | | | | X | |
|  | 70 days after final administration | | | | | |

The mean values of the serum concentration of H3-2L4 and the serum concentration of total FKN in a 2 mg/kg administration group, a 5 mg/kg administration group, a 10 mg/kg administration group, and a 15 mg/kg administration group over the administration period (12 weeks) (wherein the mean value was indicated as an arithmetical mean value) are shown in Table 9 and Table 10, respectively. In addition, transitions in the mean values of the serum concentration of H3-2L4 and the serum concentration of total FKN are shown in FIG. 2 and FIG. 3, respectively.

TABLE 9

Mean serum concentration of H3-2L4 (µg/mL) during administration period (12 weeks)

| Evaluation period | Summary statistics | Dose | | | |
|---|---|---|---|---|---|
| | | 2 mg/kg | 5 mg/kg | 10 mg/kg | 15 mg/kg |
| 1 day (at the completion of administration) | Number of subjects | 6 | 8 | 7 | 7 |
| | Mean value | 75.1 | 185 | 227 | 314 |
| | Standard deviation | 11.7 | 28.4 | 29.3 | 41.1 |
| 1 week (before administration) | Number of subjects | | | 7 | 7 |
| | Mean value | | | 82.9 | 120 |
| | Standard deviation | | | 20.4 | 34.0 |
| 1 week (at the completion of administration) | Number of subjects | | | 7 | 7 |
| | Mean value | | | 303 | 411 |
| | Standard deviation | | | 29.3 | 69.9 |
| 2 weeks (before administration) | Number of subjects | 5 | 7 | 7 | 6 |
| | Mean value | 11.5 | 31.0 | 120 | 197 |
| | Standard deviation | 4.62 | 6.75 | 31.0 | 61.1 |
| 2 weeks (at the completion of administration) | Number of subjects | 5 | 7 | 7 | 6 |
| | Mean value | 49.7 | 116 | 336 | 503 |
| | Standard deviation | 4.14 | 19.6 | 57.5 | 95.4 |
| 4 weeks (before administration) | Number of subjects | 4 | 7 | 7 | 5 |
| | Mean value | 4.90 | 29.0 | 89.6 | 164 |
| | Standard deviation | 3.37 | 10.9 | 56.3 | 71.6 |
| 4 weeks (at the completion of administration) | Number of subjects | 4 | 7 | 7 | 5 |
| | Mean value | 46.8 | 122 | 289 | 458 |
| | Standard deviation | 8.58 | 30.3 | 72.8 | 86.5 |

TABLE 9-continued

Mean serum concentration of H3-2L4 (µg/mL) during administration period (12 weeks)

| Evaluation period | Summary statistics | Dose | | | |
|---|---|---|---|---|---|
| | | 2 mg/kg | 5 mg/kg | 10 mg/kg | 15 mg/kg |
| 6 weeks (before administration) | Number of subjects | 4 | 7 | 5 | 5 |
| | Mean value | 2.92 | 26.4 | 107 | 156 |
| | Standard deviation | 3.19 | 10.6 | 57.4 | 84.9 |
| 6 weeks (at the completion of administration) | Number of subjects | 4 | 7 | 5 | 5 |
| | Mean value | 46.8 | 122 | 321 | 474 |
| | Standard deviation | 8.48 | 37.0 | 24.9 | 98.0 |
| 8 weeks (before administration) | Number of subjects | 4 | 6 | 5 | 5 |
| | Mean value | 2.65 | 28.1 | 109 | 155 |
| | Standard deviation | 3.63 | 10.6 | 59.4 | 80.6 |
| 8 weeks (at the completion of administration) | Number of subjects | 4 | 6 | 5 | 5 |
| | Mean value | 45.0 | 130 | 347 | 480 |
| | Standard deviation | 5.79 | 30.5 | 92.9 | 101 |
| 10 weeks (before administration) | Number of subjects | 3 | 6 | 5 | 5 |
| | Mean value | 3.50 | 26.5 | 110 | 147 |
| | Standard deviation | 3.75 | 9.51 | 78.8 | 84.5 |
| 10 weeks (at the completion of administration) | Number of subjects | 3 | 6 | 5 | 5 |
| | Mean value | 46.2 | 124 | 318 | 431 |
| | Standard deviation | 2.48 | 36.5 | 81.3 | 83.5 |
| 12 weeks (before administration) | Number of subjects | 3 | 6 | 5 | 5 |
| | Mean value | 3.40 | 26.1 | 96.8 | 146 |
| | Standard deviation | 3.74 | 10.4 | 60.3 | 91.9 |

TABLE 10

Serum concentration of total FKN (ng/mL) during administration period (12 weeks)

| Evaluation period | Summary statistics | Dose | | | |
|---|---|---|---|---|---|
| | | 2 mg/kg | 5 mg/kg | 10 mg/kg | 15 mg/kg |
| 1 week (before administration) | Number of subjects | | | 7 | 7 |
| | Mean value | | | 208.6 | 301.6 |
| | Standard deviation | | | 52.4 | 106.1 |
| 2 weeks (before administration) | Number of subjects | 3 | 7 | 7 | 6 |
| | Mean value | 61.9 | 119.3 | 340.9 | 455.7 |
| | Standard deviation | 28.7 | 55.0 | 109.5 | 195.8 |
| 4 weeks (before administration) | Number of subjects | 3 | 7 | 7 | 5 |
| | Mean value | 22.7 | 120.2 | 315.1 | 505.6 |
| | Standard deviation | 9.15 | 60.3 | 154.9 | 268.4 |
| 6 weeks (before administration) | Number of subjects | 3 | 7 | 5 | 5 |
| | Mean value | 13.9 | 114.2 | 410.0 | 528.8 |
| | Standard deviation | 11.7 | 66.3 | 149.6 | 324.2 |
| 8 weeks (before administration) | Number of subjects | 4 | 6 | 5 | 5 |
| | Mean value | 29.4 | 118.9 | 396.6 | 499.0 |
| | Standard deviation | 39.0 | 57.4 | 166.4 | 290.8 |
| 10 weeks (before administration) | Number of subjects | 3 | 6 | 5 | 5 |
| | Mean value | 37.3 | 110.0 | 397.0 | 486.8 |
| | Standard deviation | 38.6 | 47.3 | 142.3 | 285.1 |
| 12 weeks (before administration) | Number of subjects | 3 | 6 | 5 | 5 |
| | Mean value | 37.2 | 119.2 | 400.2 | 473.0 |
| | Standard deviation | 43.1 | 61.6 | 185.7 | 287.2 |

3-4. [Binding Occupancy]

The serum concentration of H3-2L4 and the serum concentration of total FKN obtained from the H3-2L4 single-dose administration test performed on Japanese healthy adults as targets in Example 2 were applied to two-target quasi-steady-state (QSS) models (J Pharmacokinet Pharmacodyn 2012; 39: 217-26), so that the binding affinity parameter ($K^m_{ss}$) was estimated. The binding occupancy of H3-2L4 to membrane-bound FKN (mFKN) upon repeated administration of H3-2L4 to Crohn's disease patients was simulated using the serum concentration of H3-2L4 and the $K^m_{ss}$. In addition, the concentration of free FKN (cFKN) in blood was simulated using the serum concentration of H3-2L4, the serum concentration of total FKN, and the QSS constant ($K^c_{ss}$) to cFKN. Besides, it was assumed that the QSS constant would not be changed between healthy adults and Crohn's disease patients.

Based on the simulations as described above, the binding occupancy of H3-2L4 to mFKN in each administration groups and a change in the percentage of the cFKN amount over time in each administration groups, using the cFKN amount before initiation of the administration as a baseline, are shown in FIG. 4 and FIG. 5, respectively. From these results, it has been suggested that 10 mg/kg and 15 mg/kg of the anti-fractalkine antibody be a single dose, which is effective for both binding to mFKN and inhibition against cFKN.

3-4. [Efficacy]

Efficacy was analyzed using a population of subjects who were administered with the trial drug, and as a result, had one or more of efficacy data after completion of the administration of the trial drug to be evaluated (FAS: Full Analysis Set).

The summary statistics of CDAI and CRP were calculated for individual dosages in predetermined evaluation periods.

The analysis was carried out using WinNonlin, NONMEM, SAS, etc.

[CDAI]

CDAI was calculated from the subject diary, the corresponding test results, etc., in the periods indicated with the letters X shown in the timelines (Table 7 and Table 8). Moreover, with regard to the subjects who were migrated in the continuous administration period, CDAI was further calculated every four weeks until the 52nd week in the same manner as that described above. Upon the calculation of CDAI, regarding hematocrit and body weight, the values obtained on the day of evaluation were used, whereas regarding body height, the most recent value, which was measured according to the timeline, was used.

When the CDAI score was reduced by 70 or more, from that in the observation period, it was defined as "improvement," and when the CDAI score was less than 150, it was defined as "remission."

The number of subjects in Cohorts 1 to 4 at the time of initiation of the present trial was 6 subjects, 8 subjects, 7 subjects, and 7 subjects, respectively. Until the 12th week after the first administration, the trial performed on 3 subjects, 2 subjects, 2 subjects and 2 subjects, respectively, in Cohorts 1 to 4, was terminated. It is to be noted that the subjects in Cohorts 1 to 4 had previously used the anti-TNF antibody, except for one subject in Cohort 2. The subjects who had used one agent were 2 subjects, 5 subjects, 3 subjects and 2 subjects, respectively, in Cohorts 1 to 4, whereas the subjects who had used two agents were 4 subjects, 2 subjects, 4 subjects and 5 subjects, respectively. In all of these subjects, the effects obtained by the use of the anti-TNF antibody were insufficient.

Among the subjects having a CDAI score of 220 or more before administration of the trial drug, the subjects who were confirmed to reduce the CDAI score by 70 or more (CR-70) in the evaluation at the time of the 12th week, using the CDAI score before administration of the trial drug as a baseline, were 1 subject, 2 subjects, 4 subjects and 3 subjects, respectively, in Cohorts 1 to 4. Moreover, a reduction in the CDAI score of 100 or more (CR-100) was observed in 1 subject, 1 subject, 4 subjects and 3 subjects, respectively, in Cohorts 1 to 4. Furthermore, three subjects in Cohort 3 and one subject in Cohort 4 have achieved remission. It is to be noted that three out of seven subjects in Cohort 4 had a CDAI score of 330 or greater before administration of the trial drug. When the subjects having a CDAI score of less than 330 before administration of the trial drug were categorized, a reduction of 100 or greater (CR-100) was observed in four (66%) out of six subjects in Cohort 3, and in three (75%) out of four subjects in Cohort 4. From these results, it has been suggested that 10 mg/kg and 15 mg/kg of the anti-fractalkine antibody be a single dose, which provides favorable improvement effects to Crohn's disease.

Further, the number of subjects who completed the continuous administration period was one, two, and two in Cohorts 1 to 3, respectively. Except for one subject in Cohort 2, all of the subjects who completed the continuous administration period maintained improvement effects over 52 weeks. In the evaluation at the 52nd week, 1 subject, 1 subject and 2 subjects respectively in Cohorts 1 to 3 were found to have a reduction in the CDAI score of 100 or more (CR-100), using the CDAI score before administration of the trial drug as a baseline. Still further, 2 subjects in Cohort 3 achieve remission.

Further, also in Cohort 4, three subjects, in which improvement effects had been observed in the evaluation at the time of the 12th week, were migrated to the continuous administration period. Two out of the three subjects maintained the improvement effects.

[CRP]

CRP was measured in the periods indicated with the letters X shown in the timelines (Table 7 and Table 8).

Transitions in the CRP values of 7 subjects in Cohort 3 over 12 weeks are shown in FIG. 6. Three subjects (subjects 1, 3 and 6), who had achieved remission based on the CDAI scores in the evaluation at the 12th week, were also found to have low CRP values.

What is claimed is:

1. A method for treating Crohn's disease, comprising intravenously administering to a human in need thereof multiple doses of an anti-fractalkine antibody, wherein each dose of the anti-fractalkine antibody is 10 to 15 mg/kg of human body weight, wherein the mean trough concentration of the anti-fractalkine antibody is 80 µg/mL or more, wherein the human is a Crohn's disease patient in whom prior treatment with at least one of 5-aminosalicylic acid (5-ASA), salazosulfapyridine, a corticosteroid, an immunomodulator, or an anti-TNF antibody was not effective, was initially effective but the effect became attenuated or disappeared, or could not be continued due to side effects, wherein the anti-fractalkine antibody comprises:

a heavy chain variable region comprising the amino acid sequence shown in SEQ ID NO: 13

(QVQLVQSGAEVKKPGASVKVSCKASGYTFTNYYIHWVKQAPGQGLEWIGW

IYPGDGSPKFNERFKGRTTLTADKSTNTAYMLLSSLRSEDTAVYFCATGPT

DGDYFDYWGQGTTVTVSS);

a light chain variable region comprising the amino acid sequence shown in SEQ ID NO: 14

(DIQMTQSPSSLSASVGDRVTITCRASGNIHNFLAWYQQKPGKAPKLLIYN

EKTLADGVPSRFSGSGSGTDYTLTISSLQPEDFATYFCQQFWSTPYTFGGG

TKVEIK);

and
a constant region of human IgG2 isotype, wherein
a Fc region of the constant region comprises mutations V234A and G237A.

2. The method according to claim 1, wherein the anti-fractalkine antibody is intravenously administered to the human at a dose of 10 mg/kg of human body weight or 15 mg/kg of human body weight.

3. The method according to claim 1, wherein the anti-fractalkine antibody is administered in a pharmaceutical composition that provides a mean $C_{max}$ of the anti-fractalkine antibody at a dose of 1 mg/kg of human body weight in single-dose intravenous administration with a value of 21 to 25 µg/mL.

4. The method according to claim 1, wherein the anti-fractalkine antibody is administered in a pharmaceutical composition that provides a mean $C_{max}$ of the anti-fractalkine antibody of a value included in the numerical range of 80% to 125% of $2.4 \times 10^2$ µg/mL when the anti-fractalkine antibody is administered to the human by single-dose intravenous administration at a dose of 10 mg/kg of human body weight.

5. The method according to claim 1, wherein the anti-fractalkine antibody is administered in a pharmaceutical composition that provides a mean $AUC_{(0-t)}$ of the anti-fractalkine antibody of a value included in the numerical range of 80% to 125% of $7.0 \times 10^4$ µg·h/mL when the anti-fractalkine antibody is administered to the human by single-dose intravenous administration at a dose of 10 mg/kg of human body weight.

6. The method according to claim 1, wherein the anti-fractalkine antibody is administered in a pharmaceutical composition that provides a mean $AUC_{(0-336h)}$ of the anti-fractalkine antibody of a value included in the numerical range of 80% to 125% of $3.8 \times 10^4$ µg·h/mL when the anti-fractalkine antibody is administered to the human by single-dose intravenous administration at a dose of 10 mg/kg of human body weight.

7. The method according to claim 1, which comprises multiple-dose intravenous administration of the anti-fractalkine antibody at dosing intervals from once every week to once every two weeks.

* * * * *